United States Patent
Parker et al.

(10) Patent No.: US 9,289,156 B2
(45) Date of Patent: Mar. 22, 2016

(54) LUNG FUNCTION ANALYSIS METHOD AND APPARATUS

(75) Inventors: Geoffrey Parker, Manchester (GB); Josephine Naish, Manchester (GB)

(73) Assignee: BIOxyDyn Limited, Manchester (GB)

( * ) Notice: Subject to any disclaimer, the term of this patent is extended or adjusted under 35 U.S.C. 154(b) by 489 days.

(21) Appl. No.: 13/505,608

(22) PCT Filed: Oct. 27, 2010

(86) PCT No.: PCT/GB2010/001989
§ 371 (c)(1),
(2), (4) Date: May 2, 2012

(87) PCT Pub. No.: WO2011/055105
PCT Pub. Date: May 12, 2011

(65) Prior Publication Data
US 2012/0215504 A1      Aug. 23, 2012

(30) Foreign Application Priority Data
Nov. 3, 2009 (GB) .................................. 0919269.1

(51) Int. Cl.
*G06F 17/10* (2006.01)
*A61B 5/083* (2006.01)
(Continued)

(52) U.S. Cl.
CPC .......... *A61B 5/083* (2013.01); *G01R 33/56366* (2013.01); *G01R 33/5601* (2013.01)

(58) Field of Classification Search
CPC ..... G06F 19/12; G06F 19/3437; G06F 17/10; G06F 19/321; G06F 2217/16; G06F 17/11; G06F 17/12; A61B 2019/505; A61B 17/1703; A61B 5/103; A61B 5/1114; C12Q 2537/165; G06T 2207/30004

USPC ......................................................... 703/2, 11
See application file for complete search history.

(56) References Cited

U.S. PATENT DOCUMENTS 5,694,934 A    12/1997   Edelman
6,370,415 B1    4/2002   Weiler et al.
(Continued)

FOREIGN PATENT DOCUMENTS

EP        1967138 A1   9/2008
WO        03/067216    8/2003
(Continued)

OTHER PUBLICATIONS

Brighenti et al., "A simulation model of the oxygen alveolo-capillary exchange in normal and pathological conditions", Feb. 28, 2003, Institute of Physics Publishing, Physiological Measurement, 24 (2003) 261-275.*
(Continued)

*Primary Examiner* — Omar Fernandez Rivas
*Assistant Examiner* — Shiuh-Huei Ku
(74) *Attorney, Agent, or Firm* — Michael Best & Friedrich LLP

(57) ABSTRACT

A method for generating data indicative of lung function of a subject. The method comprises receiving first data which has been obtained from the subject, and inputting said first data to a model of lung function to generate said data indicative of lung function. The model of lung function comprises a first model component modelling transfer of gaseous oxygen from a gaseous space within the lung to biological material within the lung based upon quantitative data indicative of oxygen content in the inhaled gases and oxygen content in the biological material and a second model component modelling the transfer of oxygen from the lungs by oxygenation of venous blood to create oxygenated blood based upon quantitative data indicative of oxygen content in the venous blood.

34 Claims, 5 Drawing Sheets

(51) Int. Cl.
*G01R 33/563* (2006.01)
*G06F 19/12* (2011.01)
*G06G 7/60* (2006.01)
*G01R 33/56* (2006.01)

(56) References Cited

U.S. PATENT DOCUMENTS

| | | | |
|---|---|---|---|
| 2006/0004297 A1* | 1/2006 | Orr | A61B 5/029 600/538 |
| 2007/0282214 A1 | 12/2007 | George et al. | |
| 2010/0145186 A1 | 6/2010 | McGrath et al. | |
| 2011/0035198 A1 | 2/2011 | McGrath et al. | |

FOREIGN PATENT DOCUMENTS

| | | |
|---|---|---|
| WO | 2004/070410 | 8/2004 |
| WO | 2008135712 A1 | 11/2008 |

OTHER PUBLICATIONS

Kapitan "Teaching pulmonary gas exchange physiology using computer modeling", Advances in Physiology Education, vol. 32, pp. 61-64, Mar. 2008).*

Jakob et al. "Assessment of Human Pulmonary Function Using Oxygen-Enhanced T1 Imaging in Patients with Cystic Fibrosis", Dec. 1, 2003, Magnetic Resonance in Medicine, 51:1009-1016 (2004).*

Brighenti et al. "A simulation model of the oxygen alveolo-capillary exchange in normal and pathological conditions", Feb. 28, 2003, Institute of Physics Publishing, Physiological Measurement 24 (2003) 261-275).*

Kapitan "Teaching pulmonary gas exchange physiology using computer modeling", Advanced in Physiology Education vol. 32, pp. 61-64, Mar. 2008.*

Kelman, "Digital computer subroutine for the conversion of oxygen tension into saturation", Journal of Applied Physiology, 1966, 21(4), pp. 1375-1376.

Kety, "The theory and applications of the exchange of inert gas at the lungs and tissues", Pharmacol Rev, Mar. 1951, vol. 3, No. 1, pp. 1-41.

Naish et al., "Improved Quantitative dynamic regional oxygen-enhanced pulmonary imaging using image registration", Magnetic Resonance in Medicine, Aug. 2005, 54(2), pp. 464-469.

Ohno et al., "Dynamic Oxygen-Enhanced MRI Reflects Diffusing Capacity of the Lung", Magnetic Resonance in Medicine, 2002, vol. 47, No. 6, pp. 1139-1144.

Zaharchuk et al., "Non-invasive imaging of quantitative cerebral blood flow changes during 100% oxygen inhalation using arterial spin-labeling MR imaging", American Journal of Neuroradiology, Apr. 2008, 29(4), pp. 663-667.

Office Action from the United Kingdom Intellectual Property Office for Application No. 0919269.1 dated Mar. 10, 2010 (5 pages).

* cited by examiner

LUNG FUNCTION ANALYSIS METHOD AND APPARATUS

CROSS REFERENCE TO RELATED APPLICATIONS

This application is a national phase application of PCT Application No. PCT/GB2010/001989, filed Oct. 27, 2010 which claims priority to United Kingdom Patent Application No. 0919269.1, filed Nov. 3, 2009, the entire contents of which are hereby incorporated by reference therein.

FIELD

The present invention relates to methods for generating data indicative of lung function and more particularly but not exclusively to the application of a mathematical model to data produced by oxygen-enhanced magnetic resonance imaging of a lung in order to generate further data indicative of lung function.

BACKGROUND

It will be appreciated that a clinician will wish to test lung function for a number of reasons. For example, it can be informative to characterise lung ventilation because such ventilation can be affected by a range of pulmonary disorders. Currently, standard lung function tests can assess a wide range of global variables describing lung physiology but cannot be used to investigate disease regionally within the lung.

Scintigraphy allows for investigation within a particular region of a lung by producing images of a radiation emitting material as it passes through a subject. The technique generally necessitates the inhalation of radioactive substances and is limited by low spatial resolution.

One particular example of a valuable scintigraphic imaging technique is a ventilation/perfusion (V/Q) scan, which comprises two imaging steps. First, the subject is asked to breathe a gas mixture containing a gamma radiation emitter, such as radionuclide xenon or technetium, while images of the subject's chest are recorded using a gamma camera. The resulting images show light areas in lung regions to which the gas has permeated and therefore represent information about which areas of the lungs are being ventilated and which are not. Second, an intravenous injection of a further gamma emitter, such as radioactive technetium macro aggregated albumin (Tc99m-MAA), is administered to the subject while recording further images of the subject's chest using the gamma camera. The resulting images show light areas wherever the gamma emitter has been carried within the lungs by the blood stream and therefore represent information about which regions of the lungs are being well perfused with blood. It will be appreciated that in some cases the resulting images are seen in negative, i.e. dark areas indicate higher concentrations of radiation emitting material as opposed to light areas as mentioned above.

The clinician, analysing the results of a V/Q scan may be interested in physiological parameters such as how well certain regions of the lungs are being ventilated with air or perfused with blood, but is often particularly interested in mismatches between the quality of ventilation and of perfusion in local regions in the lungs. Such mismatches indicate that gas transfer between the air and blood in the lungs is inefficient, because lung regions supplied with inhaled air are not being supplied with blood and/or lung regions supplied with blood are not being supplied with air. In the case of both chronic illnesses such as obstructive pulmonary disease and acute illnesses such as pulmonary embolism, V/Q scans are particularly valuable since they can be used to identify obstructions within the airways or blood vessels which are causing a ventilation/perfusion mismatch in a region of a lung. Unfortunately, V/Q scans provide relatively low resolution, two dimensional results (i.e. images). It will be appreciated that more local information, such as would be provided by volumetric data, would be extremely valuable in order to provide more detailed prognoses and targeted therapies for addressing ventilation/perfusion problems. Higher resolution imaging technologies, such as magnetic resonance imaging (MRI) or x-ray computed tomography (CT), have therefore been investigated for their applicability to imaging the lungs.

Oxygen-enhanced magnetic resonance imaging (OE-MRI) is a high resolution imaging technology which has been demonstrated in both healthy volunteers and patients with pulmonary disease as an alternative, indirect method to visualize lung ventilation. Molecular oxygen is paramagnetic and so acts as an MRI contrast agent when dissolved in water due to its effect on $T_1$ (which is known to those skilled in the art of MRI as the longitudinal relaxation time). Another standard output parameter of MRI is $R_1$, which is the rate of longitudinal relaxation and is therefore derivable from $T_1$ as $R_1=1/T_1$.

Oxygen is always present in a living animal body so it is not possible to use oxygen as a contrast medium in the usual way (i.e. by assuming that all visible contrast is that which has been introduced for the purposes of the study, as is the case with nuclear medicine studies). Rather, at least one baseline measurement is made while oxygen in the lung tissues is at a first concentration, and at least one contrast measurement is made while the oxygen in the lung tissues is at a second concentration. The difference between the baseline measurement(s) and the contrast measurement(s) is then calculated. Breathing 100% oxygen results in an increase in the concentration of dissolved oxygen in the water contained within both lung tissue and blood within the lungs when compared to breathing room air (at 21% oxygen), and this can be observed in data indicating the difference between the baseline measurements and the contrast measurements. More particularly, increased concentration of dissolved oxygen produces a corresponding decrease in $T_1$ which can be detected as a regional signal intensity increase in a $T_1$-weighted image, denoted here as $\Delta T_1$ (thus the difference in $R_1$ as described above is denoted $\Delta R_1$). The resulting data, $\Delta R_1$, represents the increase in dissolved oxygen concentration in the lungs.

It is possible to calculate the change in partial pressure of oxygen in a region of interest within a subject from the change in longitudinal relaxation rate $\Delta R_1$ determined by OE-MRI. An approximate average conversion factor $r_1$ between a value of $\Delta R_1$ and a value representing the partial pressure of oxygen is $r_1=2.49\times10^{-4}$ $s^{-1}mmHg^{-1}$ (Zaharchuk G, Martin A J, Dillon W P. "Noninvasive imaging of quantitative cerebral blood flow changes during 100% oxygen inhalation using arterial spin-labeling MR imaging." American Journal of Neuroradiology. April 2008; 29(4):663-7). This factor can be used to convert $\Delta R_1$ measurements to partial pressures of oxygen (in units of mmHg) by dividing each of the $\Delta R_1$ values generated by an OE-MRI study by the conversion factor $r_1$, i.e. $\Delta PW_{O2}=\Delta R_1/r_1$, where $\Delta PW_{O2}$ is the change in partial pressure of oxygen in units of millimeters of mercury (mmHg) in tissue water. It is known to perform a plurality of scans, i.e. a "study", on the same patient over a short time scale so as to produce a dataset which represents the change in partial pressure of oxygen in a number of local regions of interest within the subject's lungs over the period of the study.

High resolution analysis of the lungs by multiple OE-MRI scans over time is made difficult by the change in size and shape of the lungs from one image to the next due to breathing. Breath-holding has been used in some studies but in patients with lung disease this can be uncomfortable and, as a result, difficult to perform in a reproducible manner. It may also be argued that breath-holding interferes with the phenomena being assessed since it requires large static inhalations which may lead to spurious interpretation of normal breathing function. Accordingly image registration methods have been developed to correct for breathing motion before calculation of $\Delta R_1$ (e.g. see Naish et al. (2005) Magnetic Resonance in Medicine 54:464-469). Such methods allow registration of a lung outline such that data resulting from multiple scans of the same subject over time can be registered together with the result that data values relating to corresponding locations within the subject's lungs are identifiable as such. Moreover, registration of datasets between different subjects may allow comparison of lung function between the subjects in such a way that differing lung sizes and shapes are at least partially accounted for.

Each data value produced by an OE-MRI scan as described above relates to the change in partial pressure of oxygen for a single point in time. Even when a study is performed, i.e. a plurality of scans over a given time period, the results are a number of scalar data values for a plurality of time points. It is not therefore possible to directly measure desired aspects function of the lung, using such a method. If a method could be found to utilise the data values produced by an OE-MRI study so as to infer functional information about a subject then functional data could be determined at OE-MRI resolutions over the region of the lungs. This data would be extremely useful in diagnosis and prognostic estimation for people or animals.

An existing method of generating functional data about the lungs from OE-MRI data is to begin by constructing a simple, highly abstracted functional model comprising model parameters the values of which are expected to change in response to a change in lung function. The model is then "fitted" to data generated for a subject over time for a region of interest. The fitting can take many forms, but its general purpose is to apply the model to the data so as to determine values for one or more model parameters which result in the model representing the data with acceptable accuracy. The values of the model parameters which have been determined by the fitting are then used to compare lung function between subjects or between datasets acquired from the same subject over time.

Such a model is validated by gathering empirical evidence that, once fitted to data, the model provides a set of data values which have diagnostic capability. That is, the value of at least one parameter of the model changes depending on the health and/or particular diagnosis of the subject. The values produced by such a model are not, however, suitable for quantitative analysis of lung function because none of the model parameters relate directly to measurable physiological parameters. Rather, the model parameters are abstract indicators which have been arrived at by roughly approximating physiological function.

SUMMARY

It is an object of the present invention to obviate or mitigate at least one of the problems described above.

According to a first aspect of the invention there is provided a method for generating data indicative of lung function of a subject, the method comprising receiving first data which has been obtained from the subject and inputting said first data to a model of lung function to generate said data indicative of lung function; wherein the model of lung function comprises a first model component modelling transfer of gaseous oxygen from a gaseous space within the lung to biological material within the lung based upon quantitative data indicative of oxygen content in the inhaled gases and oxygen content in the biological material, and a second model component modelling the transfer of oxygen from the lungs by oxygenation of venous blood to create oxygenated blood based upon quantitative data indicative of oxygen content in the venous blood.

The method according to the first aspect of the present invention is advantageous in that the first and second model components provide improved model accuracy by considering both the oxygen content in the biological material in the lungs and in the venous blood respectively. It has been realised that the consideration of these two particular concentrations of oxygen in the model allows sufficiently accurate modelling of lung function so as to produce data indicative of lung function.

Biological material in the context of the invention means the non-gaseous matter which makes up the lung. More particularly, biological material includes blood and tissues, whether lung tissues (or parenchyma), blood vessels or other tissues including cancerous tissue. Biological material may also include non-blood body fluids. Gaseous spaces and alveolar spaces in the context of the invention mean non-solid and non-liquid spaces within the lungs. More particularly, gaseous spaces and alveolar spaces include bronchi, bronchioli, alveoli, alveolar ducts and alveolar sacs within the lungs.

The quantity of data indicative of oxygen content in the inhaled gases may be indicative of a change of oxygen content in the inhaled gases. The quantitative data indicative of oxygen content in the biological material may be indicative of a change of oxygen content in the biological material. The quantitative data indicative of oxygen content in the venous blood may be indicative of a change of oxygen content in the venous blood.

The second model component may comprise a first parameter representing a volume of blood flow. The generated data may include at least one value for said first parameter representing a volume of blood flow. The use of this first parameter is advantageous in that the model can either receive data which has been determined about blood flow in the subject as an input to the model or, preferably, can produce quantitative data about blood flow from the model. The first model parameter can be expressed in units of volume of blood per volume of lung per unit of time.

The first model component may comprise a second parameter representing a volume of inhaled gases in at least part of the gaseous space. The generated data may include at least one value for said second parameter representing a volume of inhaled gases in at least part of the gaseous space. The use of this second parameter is advantageous in that the model can either receive data which has been determined about the volume of gas inhaled by the subject as an input to the model or can produce quantitative data about volumes of inhaled gas within the lung from the model.

The method according to the first aspect of the present invention may further comprise generating data based upon said first parameter and second parameter. Generating data based upon said first parameter and said second parameter may comprise performing an arithmetic operation on a value of said first parameter and a value of said second parameter. The arithmetic operation may be a division of a ventilation value based upon said second parameter by a perfusion value based upon said first parameter.

As described above, information about ventilation and perfusion, and particularly ventilation/perfusion mismatch, is extremely valuable in a clinical setting. An advantage of a model which is based upon the movement of blood and air within the lungs (rather than the movement of a radiation emitting contrast medium) is that the model is capable of producing quantitative values which can be compared against known statistical averages, compared between patients or compared between multiple scans of the same patient over time. Known V/Q scans are not suitable for this kind of quantitative comparison due to the unpredictability of the movement of the contrast. Rather, the images which result from known V/Q scans are assessed or compared visually by a clinician.

The model of lung function may model lung function in a part of a lung comprising a first portion comprising said gaseous space and a second portion comprising said biological material. The first parameter may represent a volume of blood flow thorough said second portion of the part of the lung. The second parameter may represent the volume of inhaled gasses in the first portion of the part of the lung.

The quantitative data indicative of oxygen content in the venous blood may comprise a plurality of values each relating to oxygen content at a respective time. The method may further comprise receiving the quantitative data indicative of oxygen content (or change in oxygen content) in the venous blood, the quantitative data indicative of oxygen content in the venous blood having been obtained from the subject. That is, a test or tests may be carried out on the subject to determine quantitative data indicative of oxygen content in the venous blood.

The model may include a component representing the solubility of oxygen in blood. The component representing the solubility of oxygen in blood may be based on a dissociation curve of oxygen-haemoglobin saturation. The model may approximate the solubility of oxygen in the blood using a linear function, or alternatively a quadratic function or a spline.

The first model component may comprise a first part representing the amount of inhaled gases. The first model component may further comprise a second part representing the amount of oxygen diffused into the biological material from the gaseous space. The first model component may be defined by a difference between said first part and said second part of said first model component.

The second model component may comprise a first part representing the amount of oxygen diffused into the biological material from the gaseous space. The second model component may further comprise a second part representing the transfer of oxygen from the lungs by oxygenation of venous blood. The second model component may be defined by a difference between said first part and said second part of said second model component.

The model may assume that the concentration of oxygen in the gaseous space within the lung is substantially proportional, by a known constant of proportionality, to the oxygen concentration in the biological material within the lung. The model may assume that the concentration of oxygen in the gaseous space within the lung is substantially equal to the concentration of oxygen in the biological material.

The model may comprise a third parameter indicating a proportion of a part of the lung made up of one of said first and second portions. The method according to the first aspect of the present invention may further comprise receiving at least one value for the third parameter as an input. The at least one value for the third parameter may have been obtained from the subject. That is, data (e.g. image data) may be obtained from the subject to generate the value for the third parameter. The data may be obtained by any appropriate method, including by an x-ray computed tomography scan or a magnetic resonance proton density scan.

The first and second model components may be combined together in the model according to said proportion. The model may have the form:

$$\left(\frac{(1-v_W)}{PB - P_{H_2O}} + v_W \alpha'_{O_2}\right)\frac{dPw_{O_2}}{dt} =$$
$$\dot{V}_A\left(FI_{O_2} - \frac{Pw_{O_2}}{PB - P_{H_2O}}\right) - \dot{Q}(Co + \beta w_{O_2} - C\bar{v}_{O_2})$$

wherein $Pw_{O_2}$ is an input parameter representing the partial pressure of oxygen in the biological material in said part of the lung; $FI_{O_2}$ is an input parameter representing the concentration of oxygen inhaled by the subject; $C\bar{v}_{O_2}$ is an input parameter representing the concentration of oxygen present in the venous system of the subject; $\alpha_{O_2}'$ is an input parameter which represents the solubility of oxygen in the biological material; $\beta_{O_2}$ is an input parameter which represents the solubility coefficient of oxygen in the blood which may be approximated by a linear relationship with respect to the partial pressure of dissolved oxygen $Pw_{O_2}$ over a typical range of partial pressures observed during a study; $v_W$ is a parameter representing the proportion of biological material in said part of the lung, $\dot{V}_A$ is an output parameter for the model which represents the volume of inhaled gases within said gaseous space in said part of the lung; Co is an extrapolation of the concentration of oxygen in blood at zero partial pressure based upon the linear relationship used to determine $\beta_{O_2}$; and $\dot{Q}$ is an output parameter for the model which represents the volume of blood which passes through said part of the lung.

A model of the general type described above may be processed to integrate the term indicating a rate of change of the partial pressure with respect to time (i.e. to eliminate the term $$\frac{dPw_{O_2}}{dt}\bigg).$$

This integration may result in the replacement of that term with terms indicating measurements of partial pressure oxygen within the biological material at a plurality of time points. This is useful in that data indicating measurements of the partial pressure of oxygen in the biological material at a plurality of time points is data which can more readily be obtained from OE-MRI data. The elimination of the rate of change term can be carried out in any convenient way. For example, an integrating factor may be used to perform the elimination.

One advantage of some embodiments of the invention is the use of mathematical models that include parameters which correspond to standard physiological parameters, e.g. of lung function. In particular, mathematical models according to some embodiments of the invention include model parameters for at least one of, or some combination of: the volume of alveolar gas in units of volume of gas per unit time per unit volume of lung, the systemic (non-local) venous oxygen concentration (i.e. the concentration of oxygen in the blood arriving at the lungs) in units of volume of gas per unit volume of blood, the capillary blood flow through a particular region of interest in units of volume of blood per unit of time per unit volume of lung, and the solubility of oxygen in blood (whole blood including blood plasma) in units of volume of oxygen per volume of blood for a given pressure.

A model which incorporates physiologically accurate model parameters is necessarily complex because the physiology which is being modelled is complex. It is difficult to apply such a model to a real situation since the model has a large number of unknowns. The inventors have realised that it is possible to start with such a complex model and simplify it in such a way that the resulting simplified model remains clinically significant and contains accepted physiological parameters. If one or more measurements are made of some of the model parameters then these parameters do not need to be fitted to the data but become inputs to the model and/or if assumptions are made with regard to certain parameters of the model then these parameters also do not need to be fitted to the data. Critically, simplification of the complex model in this way using known assumptions and clinically acceptable measurements maintains the clinical significance of the remaining modelled parameters. Moreover, any assumptions are made in relation to known physiological parameters and the validity of the assumptions can be verified against the literature. Therefore, the resulting simplified model is delivered with a known set of validated assumptions which can be used to validate the results ultimately generated by fitting the simplified model to the data.

The quantitative data indicative of oxygen content in the biological material may be based upon oxygen enhanced magnetic resonance data. The generation of data indicative of lung function in the method according to the first aspect of the invention may comprise application of the Levenberg Marquardt non-linear least squares fitting algorithm or other fitting algorithm to the model so as to fit said model to said input data.

According to a second aspect of the invention, there is provided a method for generating data indicative of ventilation and perfusion within a subject's lung the method comprising obtaining first data indicative of ventilation and perfusion while the subject inhales gases comprising a first concentration of oxygen; obtaining second data indicative of ventilation and perfusion while the subject inhales gases comprising a second concentration of oxygen; generating third data based upon the first and second data; and determining quantitative data indicative of ventilation and perfusion based upon the third data.

An advantage of the method according to the second aspect of the invention is that by obtaining data while the subject inhales two different concentrations of oxygen quantitative data indicative of ventilation and perfusion can be determined, while traditional methods are limited to determining non-quantitative information about ventilation and perfusion determined indirectly from the propagation of contrast materials which are not normally present within the lungs.

The first concentration of oxygen may be approximately 21%, i.e. the concentration normally present in atmospheric air, and/or the second concentration of oxygen may be approximately 100%. The first and/or second data may be magnetic resonance data obtained from the subject. In general terms, the data obtained according to the second aspect of the invention may be obtained by an oxygen-enhanced magnetic resonance study, the parameters for which may be any desirable parameters for obtaining such data. It will be appreciated that it is not necessary to instantaneously switch between the different concentrations of oxygen breathed by the subject (21% and 100% in the above example). Indeed, the only requirement is that the concentration of oxygen breathed by the subject varies over time and that the concentration breathed by the subject at any given time is known.

The determining may comprise processing the third data using a mathematical model. The processing may comprise determining at least one value of a parameter of the mathematical model based upon said third data.

The mathematical model of the second aspect of the present invention may comprise a first model component modelling transfer of gaseous oxygen from a gaseous space within the lung to biological material within the lung based upon quantitative data indicative of oxygen content in the inhaled gases and oxygen content in the biological material and a second model component modelling the transfer of oxygen from the lungs by oxygenation of venous blood to create oxygenated blood based upon quantitative data indicative of oxygen content in the venous blood.

The mathematical model of the second aspect of the invention may comprise any of the features of the first aspect of the invention.

Subjects tested according to the methods of the invention may be any subject for which it is desirable to test lung function. The subject may be a mammal (although the methodology is also generally applicable to any organism with a lung). The subject may be a human.

The methods are particularly useful for testing human subjects with conditions such as pulmonary embolism, asthma, COPD, fibrotic lung diseases, emphysema, bronchitis, alpha1-antitrypsine deficiency or bronchiectasis; or in the case of airway constriction or alveolar damage caused by smoking or environmental factors. Such human subjects are known to have impaired lung function and providing an indication of the extent of the impairment in each of a plurality of local regions within the lung is a valuable measurement which may determine the approach to treatment of each human subject.

It is preferred that an OE-MRI study is used to gather a plurality of data values about oxygen partial pressure changes from various regions of interest within the lungs of a subject. It will of course be appreciated that the applicability of the mathematical model is not limited to use with OE-MRI data and may be combined with other imaging methodologies and/or diagnostic medical tests. In the preferred embodiment using OE-MRI, subjects to be tested should be placed in an MRI machine typically but not necessarily at 1.5 tesla magnetic field strength. As the method requires little specialist equipment it should be possible to use OE-MRI in any MRI machine designed for human or animal use. A $T_1$-weighted imaging protocol should be chosen which is suitable for lung imaging, i.e. which can overcome the problems caused by low proton density in the lung and the magnetic field inhomogeneity induced by the many air-tissue interfaces of the lung, and one which is also sufficiently sensitive to the signal changes induced by changes in inhaled oxygen concentration, e.g. an Inversion Recovery Half Fourier Single-Shot Turbo Spin-Echo (IR-HASTE) sequence, or an Inversion Recovery Snapshot Fast Low Angle-Shot (IR Snapshot FLASH) sequence. Gases are typically delivered at a rate of 10-15 l/min.

In one embodiment, during a study, the subject inhales gases with at least two different partial pressures of a paramagnetic gas (e.g. oxygen), and may be fitted with a mask or breathing apparatus for gas delivery in order that different gases may be inhaled while the MRI scans are performed. When the gas is oxygen room air may be used as one of the partial pressures of oxygen in which instance the subject would breathe normally without the use of any apparatus. In some embodiments medical air, which mimics room air but is administered from a controlled source is used as it is easier to switch between one administered gas and another than to switch between a non-administered source (i.e. normally breathed room air) and an administered source.

It is preferred that the subject inhales two gases—a first gas which comprises a relatively low concentration of oxygen (e.g. 10%-35%) and a second gas which comprises a relatively high concentration of oxygen (e.g. 45%-100%). It is most preferred that the first gas is air (comprising approximately 21% oxygen) and the other is a gas comprising an oxygen content of 90%-100%. It will be appreciated that the choice of gases used may depend on the health status of the subject.

The subject may revert back to breathing the first gas. In this event, measurements are preferably made which detect the change in concentration of dissolved oxygen within the lungs during this further transition period. Transitions between each gas may be repeated as needed.

It is preferred that OE-MRI data is recorded for each region of interest within the lungs by starting a subject on a low concentration of oxygen then swapping the inhaled gas to one with a high oxygen concentration for a period of time. The method of the invention most preferably generates OE-MRI data from a subject when the subject is breathing normal air (e.g. medical air comprising 21% oxygen) and 100% oxygen. The differing concentrations of the oxygen, acting as a contrast medium, then influence the MRI signal detected from protons (primarily from the hydrogen nuclei found in water or lipids in the pulmonary tissue) if proton MRI is being employed but potentially other MRI-visible nuclei if non-proton MRI is being employed, and this OE-MRI data is then used to create the input for the model.

In a subject with healthy lung function the Oxygen-Enhanced MRI signal of the lung will have increased and reached saturation within approximately 5 min of the subject beginning to inhale 100% oxygen. The time for the signal to decrease to its normal baseline value when the gases are switched back to air is also within the same time frame of approximately 5 min. Typically the subject will be required to breathe a gas mixture or mixtures with a higher concentration of oxygen for a maximum period of approximately 10 minutes. Adverse effects from breathing higher concentrations of oxygen have only been noted in healthy subjects after approximately 24 hours exposure, and therefore this length of exposure is deemed safe and without any detrimental effects for the majority of subjects. In patients with serious lung disorders, such as COPD, the effect of breathing 100% oxygen can be detrimental due to the effects of oxygen driven breathing, which is a known complication in illnesses such as COPD. In subjects whose breathing is driven by oxygen, an increase in the concentration of oxygen breathed results in a decreased impulse to continue to breathe and can have serious consequences. It will therefore be appreciated that the duration of the study is chosen for its balance between subject comfort and safety, and data quality. It will further be appreciated that, as with all medical studies, some subjects may not be able to safely undergo the OE-MRI study.

The models according to some embodiments of the invention, once constructed, may be solved numerically using any algorithm (such as the Levenberg Marquardt non-linear least squares fitting algorithm) that allows the fitting of a functional form, as defined by the compartmental model, to the dataset produced by the study, for example, by the OE-MRI. Techniques for fitting functions to measurements are known in the art.

The models according to the invention may be an adaptation of the equations developed by Kety (Kety, S S (1951) Pharmacological Reviews. 3: 1-41) who described the rate of diffusion of gases across the alveolus membrane to pulmonary capillary blood.

Throughout the specification, any reference to the volume of gases is given at body temperature and pressure, saturated with water vapour (i.e. BTPS).

The aspects of the invention described above can be implemented in any convenient way, including by way of methods, apparatus and computer programs. The invention therefore provides computer programs comprising computer readable instructions which cause a computer to carry out the methods described above. Such computer programs can be carried on any suitable computer readable medium including tangible media (e.g. disks) and intangible media (e.g. communications signals). The invention also provides apparatus programmed to carry out the methods described above.

It will be appreciated that features described in the context of one aspect of the invention can be applied to the other aspect of the invention.

BRIEF DESCRIPTION OF THE DRAWINGS

Embodiments of the invention are now described, by way of example only, with reference to the accompanying drawings, in which.

DETAILED DESCRIPTION

Figure 1:
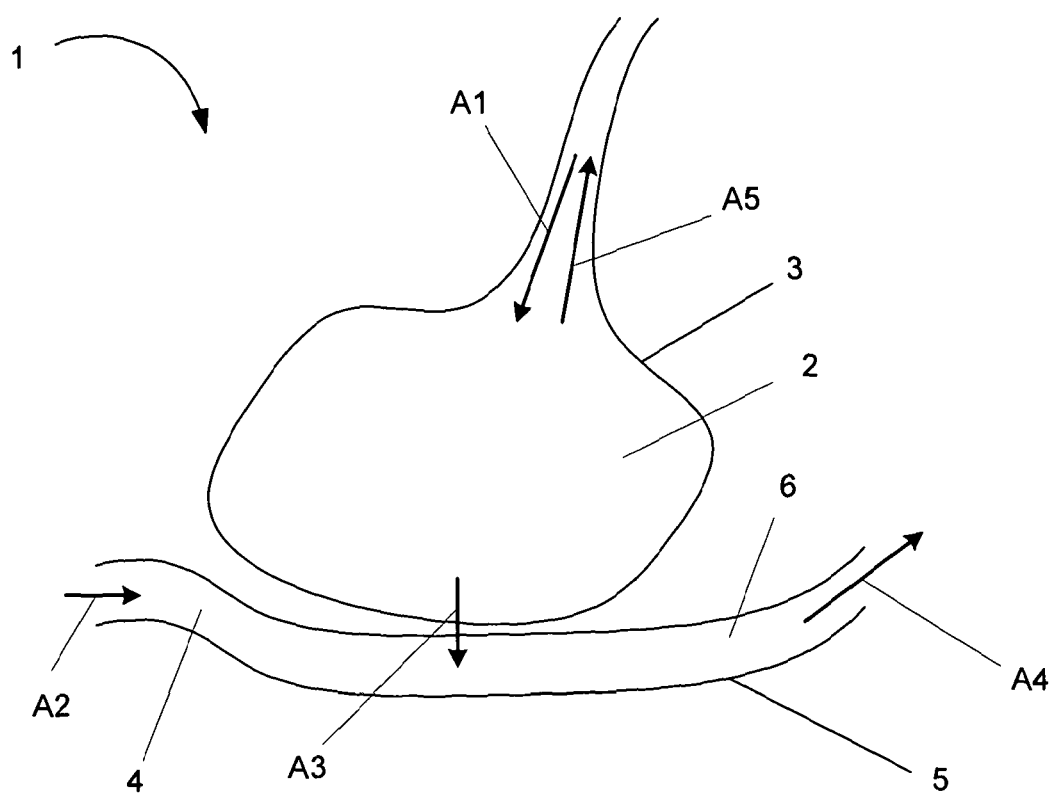
FIG. 1 is a diagrammatic representation of the transit of oxygen into a human body through the lungs.

FIG. 1 shows a region of interest within a lung 1. Air 2 is inhaled into the lung 1 and inflates an alveolus 3 within the region of interest as indicated by an arrow A1. Deoxygenated blood 4 flows into the lung 1 from the venous system (not shown), as indicated by an arrow A2. The blood 4 is carried by a capillary 5 in the lung 1 past the alveolus 3, where the deoxygenated blood 4 is oxygenated by gas transfer (indicated by an arrow A3) between the air 2 in the alveolus 3 and the blood 4 in the capillary 5 to form oxygenated blood 6. The oxygenated blood 6 is then transported away from the lung 1 as indicated by an arrow A4. The alveolus 2 then deflates as the air 2 leaves the alveolus (indicated by an arrow A5) during exhalation of the air 2 from the lung 1.

Figure 2:
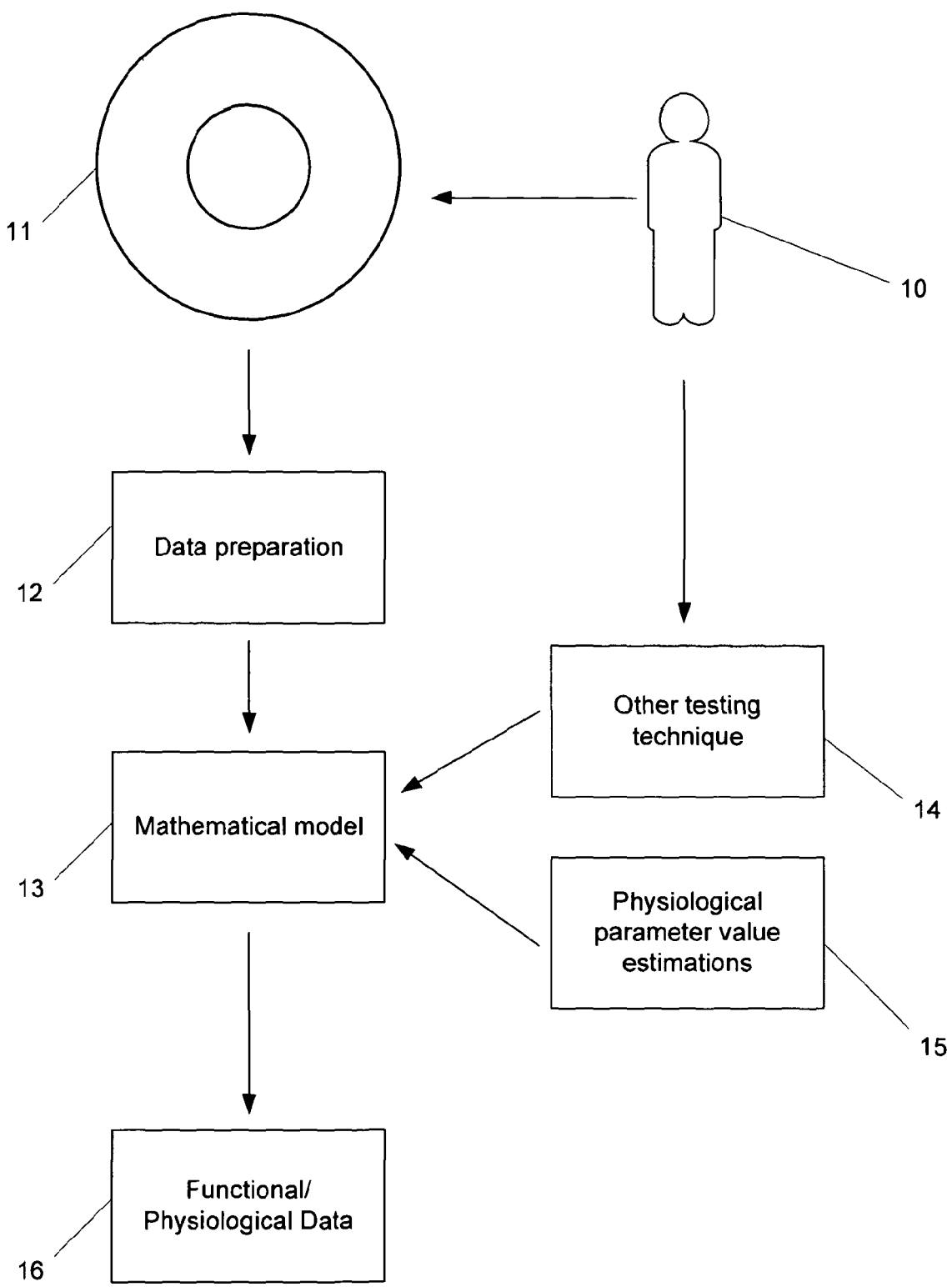
FIG. 2 is a diagrammatic representation of the components of an embodiment of an imaging technique in accordance with an aspect of the present invention.

In order to determine values of at least some of the physiological parameters described in relation to FIG. 1 for a particular subject 10, an imaging technique is performed on the subject 10 as depicted in FIG. 2. First, the subject 10 is placed inside a magnetic resonance scanner 11 and an imaging study is performed while the subject breathes first air having an oxygen concentration of about 21% and then breathes 100% oxygen.

The study comprises a number of individual scans, each of which generates at least one data value for each of a plurality of regions of interest within the lungs of the subject 10. At least one of the scans relates to the lungs before the subject 10 starts breathing the 100% oxygen. It will be appreciated that, generally, performing more scans while the subject breathes the baseline concentration of oxygen (i.e. 21%) can improve the imaging technique results because the data produced by those scans for each region of interest are indicative of normal (i.e. non-contrast enhanced) MR signal strengths in the subject and can be combined, for example by averaging. The regions of interest within the lungs are notionally adjacent to one another and arranged in a three dimensional (3D) grid so that the OE-MRI study produces a four dimensional (4D) dataset (i.e. three spatial dimensions plus time).

The dataset is input to a data preparation module 12. The data preparation module 12 applies a registration algorithm to the dataset so as to generate a registered dataset in which each spatial location in the dataset contains a plurality of data values (one for each time point) relating to the MR signal during the study at a corresponding spatial location within the lungs. That is, a value of $R_1$ representing magnetic resonance longitudinal relaxation rate measured at a given location (x,y,z) in the lung at a given time t may be found in the 4D dataset at l(x,y,z,t), and a value of $R_1$ for the same location within the lungs for the following time point is given by the location l(x,y,z,t+1) in the dataset. Thus, for a given location within the lungs, the registered dataset contains a plurality of values (at the same x,y,z co-ordinates in each dataset) of $R_1$ for each of a plurality of time points during the OE-MRI study. The data preparation module 12 then subtracts a value of $R_1$ determined for each regional lung location (x,y,z) when the subject was breathing air having an oxygen concentration of 21% (the values being determined from the at least one scan taken before the subject started breathing 100% oxygen) from the corresponding spatial location in the dataset for each time point. The $\Delta R_1$ values in the resulting dataset are then converted to values indicative of the change in partial pressure of oxygen using a conversion factor, such as $r_1 = 2.49 \times 10^{-4}$ $s^{-1}mmHg^{-1}$ as determined by Zaharchuk, Martin and Dillon as described above. Accordingly, the output from the data preparation module is a 4D dataset containing data values representing the increased dissolved oxygen concentration in each of a plurality of adjacent regions of interest within the lungs over time. Gaseous oxygen within the alveolar spaces in the lungs, such as that in the air in the alveolus 3, is not visible to OE-MRI. This is because it is the effect on water in which the oxygen is dissolved, and not the oxygen itself, which is detected by OE-MRI. The values of change in partial pressure data values in the 4D dataset are therefore representative of the change in partial pressure only of dissolved oxygen, and not gaseous oxygen, in the region of interest.

Data values l(x,y,z,t) for all times t from the dataset which correspond to a given spatial location (x,y,z) within the lungs are input to a mathematical model 13, described in detail further below. Other measurements or tests 14 may be performed upon the subject 10 so as to determine other data values which may be input to the model 13. The measurements 14 may be of a physiological parameter which does not (or is not deemed to) change over time, or may change over time and therefore be measured for each of a plurality of time points corresponding to the time points of the scans of the OE-MRI study described above. Other inputs may be made to the model by making estimations 15 of the values of certain parameters for each of the time points. It will be appreciated that in some embodiments the further measurements 14 are not needed. Once all data value inputs have been fed into the model, a fitting operation is performed in which values 16 are determined for any remaining model parameters (i.e. unknowns). The values 16 determined for the remaining model parameters are the output from the imaging technique and represent physiological parameters of the lung function of the subject.

Figure 3:
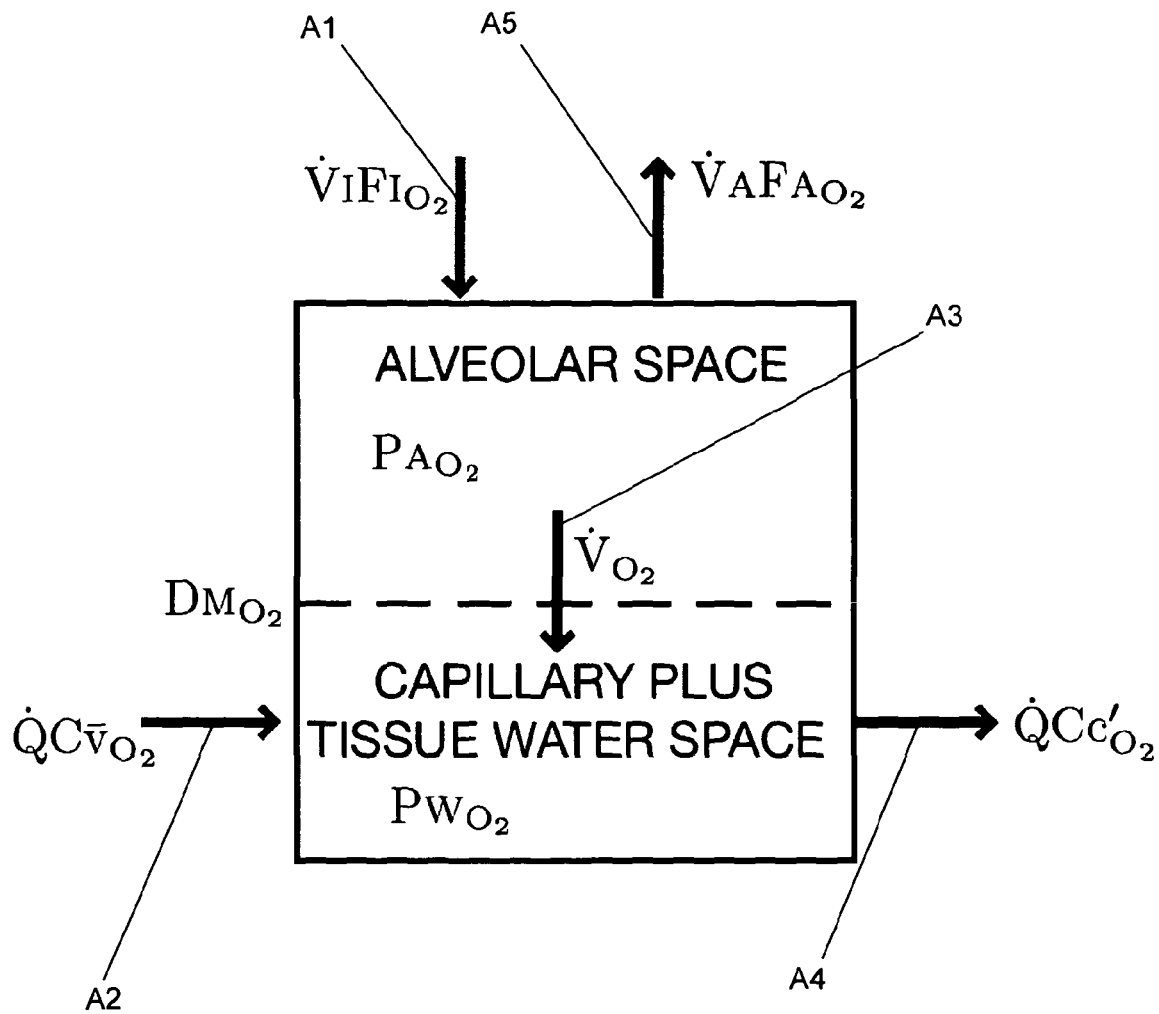
FIG. 3 is a diagrammatic representation of the relationship between the parameters of an embodiment of a model in accordance with the present invention.

The nature of the mathematical model 13, into which the input data values are fed and from which output values 16 are generated, is determinative to the usability of the output values. A model containing model parameters the values of which can be related to, and verified against, known values of related physiological parameters may be used to quantitatively assess lung function in the subject. In contrast, a model without such verifiable parameters may not be used in this way (although such a model may remain useful in distinguishing between healthy and unhealthy lung function). The following description relates to an implementation of the mathematical model 13 which may readily be used in relation to the above imaging technique In general terms the mathematical model (or models) 13 provides terms which represent at least some of the parameters of the spaces and the transfers of oxygen between the spaces depicted in FIG. 1. In each of the spaces within the lung 1 the concentration of oxygen is not uniform; by which it is meant that, for example, the air 2 in the alveolus 3 may not have a uniform distribution of oxygen during inhalation, diffusion or exhalation. Rather the oxygen concentration fluctuates across the space. However, as shown in FIG. 3, the spaces in the lung shown in FIG. 1 can be modelled as a system in which it is assumed that, within each of the spaces, there is a uniform oxygen concentration. For example, $Pw_{O_2}$ is the partial pressure of oxygen dissolved in the blood and tissues in a region of interest, which is assumed to be uniform throughout the blood and tissues within a particular region of interest. It will be noted that all of the transfers indicated by arrows in FIG. 1 are replicated by correspondingly labelled arrows in the schematic illustration of the model in FIG. 3. It will of course be appreciated that not all of the transfers need to be considered by a model in accordance with the invention in order for the model to produce meaningful data indicative of lung function.

In any given time period the net input of gaseous oxygen (which, as explained above, is not OE-MRI visible) into the alveolar spaces 3 can be modelled as the difference in oxygen concentration between gas entering the alveolar spaces (denoted by the arrow A1) and gas leaving the alveolar spaces (denoted by the arrow A5), taking into account the difference in the volume of gas entering and leaving the alveolar spaces, in other words:

$$d\dot{I}_{O_2} = \dot{V}_I F_{I_{O_2}} - \dot{V}_A F_{A_{O_2}} \quad (1)$$

where $d\dot{I}_{O_2}$ is a numerical value which represents the net volume of oxygen input into the alveolar spaces within the lungs in units of ml $O_2$/min/ml lungs; $\dot{V}_I$ is a value which represents the volume of inspired oxygen entering the alveolar spaces in units of ml gas/min/ml lungs; $\dot{V}_A$ is a value which represents the volume of expired oxygen leaving the alveolar spaces in units of ml gas/min/ml lungs; $FI_{O_2}$ is a value between 0 and 1 which represents the fractional concentration of oxygen in the inspired gas; and $F_{A_{O_2}}$ is a value between 0 and 1 which represents the fractional concentration of oxygen in the expired gas. $\dot{V}_I$, $\dot{V}_A$, $FI_{O_2}$ and $F_{A_{O_2}}$ are shown in FIG. 3.

Although in reality a subject breathes out a small amount less than is breathed in, it is reasonable to assume that the volumes inspired and expired (i.e. $\dot{V}_I$ and $\dot{V}_A$ indicated by arrows A1 and A5 respectively) are equal. Accordingly:

$$dI_{O_2} = \dot{V}_A(F_{I_{O_2}} - F_{A_{O_2}}) \quad (2)$$

It will be appreciated that this assumption can be made more general by expressing $\dot{V}_I$ in terms of multiples of $\dot{V}_A$ rather than by restricting the relationship to an equality.

Oxygen within the alveoli is diffused (as indicated by the arrow A3) into water within nearby tissues 2, and blood 6 in the nearby capillary 5 (tissue, blood vessels and blood within the lungs are generally referred to herein as biological material). At this point the oxygen becomes MR visible since it is now dissolved in water. Some of the oxygen dissolved into this water is immediately bonded to haemoglobin in the oxygenated blood 6, at which point the bonded oxygen again becomes invisible to MR. Using Fick's diffusion law, the oxygen input into the deoxygenated blood 4 and tissue water from the alveolar spaces can be described as:

$$\dot{V}_{O_2} = D_{M_{O_2}}(P_{A_{O_2}} - P_{W_{O_2}}) \quad (3)$$

where $\dot{V}_{O_2}$ is a value which represents the volume of oxygen diffused into the water in units of ml $O_2$/min/ml lung 1; $P_{A_{O_2}}$ is a value which represents the partial pressure of oxygen in the alveolar spaces in units of mmHg; and $P_{W_{O_2}}$ is a value which represents the partial pressure of oxygen dissolved in the water in units of mmHg. $\dot{V}_{O_2}$, $P_{A_{O_2}}$ and $P_{W_{O_2}}$ are shown in FIG. 3.

$D_{M_{O_2}}$ (denoted in FIG. 3 at the boundary of the alveolar space and the biological material) is the diffusion coefficient for oxygen into the water given by:

$$DM_{O_2} = \frac{D_{O_2} S \alpha_{O_2}}{H} \quad (4)$$

where $D_{O_2}$ is a value which represents the diffusion coefficient for the volume of oxygen diffused through the membranes which border the alveolar spaces in units of $cm^2/s$; S is the surface area of membranes per unit volume in units of mm/ml lung 1; $\alpha_{O_2}$ is the solubility coefficient of oxygen in the solvent of the membrane (i.e. the membrane water) in units of ml $O_2$/ml water; and H is the thickness of the membrane in units of mm.

The change in fractional oxygen concentration in an alveolar space ($dF_{A_{O_2}}$) can be defined as the input oxygen into the alveolar space due to breathing as set out in equation 2 less the output oxygen from the alveolar space due to diffusion as set out in equation 3. This is set out in equation 5:

$$v_A \frac{dFA_{O_2}}{dt} = \dot{V}A(FI_{O_2} - FA_{O_2}) - DM_{O_2}(PA_{O_2} - PW_{O_2}) \quad (5)$$

where $v_A$ is a value between 0 and 1 which represents the proportion of the whole space (including biological material and alveolar gas spaces) which is taken up by gas space; t is a value which represents time; and the equation is thus a differential which represents the change in oxygen concentration in the alveolar spaces (such as within the alveolus 3) for a change in time t.

So as to create a relationship between the input and output parts of equation 5, it is desirable to convert the fractional concentration of inspired oxygen into a partial pressure representing gaseous oxygen partial pressure in the lung 1. This can be achieved by considering the composition of the air 2 in the alveolar spaces in terms of partial pressures. It is known that the air 2 in the alveolar spaces should be at roughly barometric pressure (760 mmHg) and that the air 2 should carry a certain amount of water vapour. Oxygen dissolved in water vapour in the air 2 would not be diffused into blood 4 in the capillary 5 and so it is not desirable to consider this in the calculation of the partial pressure of oxygen in the space. Equation 6 defines the conversion between fractional concentrations of a gas, such as $FA_{O_2}$, and partial pressures which are more readily usable and verifiable in a clinical setting:

$$FA_{O_2} = \frac{PA_{O_2}}{(PB - P_{H_2O})} \quad (6)$$

where PB is the barometric (i.e. atmospheric) pressure, which is approximately 760 mmHg; and $P_{H_2O}$ is the partial pressure of water vapour, which at body temperatures is known to be approximately 47 mmHg.

Substituting equation 6 into equation 5 gives:

$$\frac{v_A}{PB - P_{H_2O}} \frac{dPA_{O_2}}{dt} = \dot{V}A\left(FI_{O_2} - \frac{PA_{O_2}}{PB - P_{H_2O}}\right) - DM_{O_2}(PA_{O_2} - PW_{O_2}) \quad (7)$$

In equation 7, the fractional concentration of oxygen input $FI_{O_2}$ is not converted into partial pressures. This is because the concentration of oxygen breathed by the subject is often known in fractional concentrations (e.g. 21% $O_2$ for room air). It will be appreciated that in some circumstances rather than estimating the fractional concentration of oxygen breathed by a subject, it is desirable to measure the partial pressure inhaled, for example by means of a gas analyser or the like.

In addition to the model of net input to the alveolar gas spaces from breathing, as given in equation 7, the net input of oxygen into the blood 4 and tissue water from the gas spaces can be modelled using standard physiological parameters as is now described.

Recalling equation 3:

$$\dot{V}_{O_2} = D_{M_{O_2}}(P_{A_{O_2}} - P_{W_{O_2}}) \quad (3)$$

It is known from equation 3 that the gross input of oxygen into the blood 4 and tissue water from the alveolar gas spaces (at arrow A3) is given by Fick's law of diffusion. The gross output of oxygen from the lung 1 is made up from oxygen which is carried away (at arrow A4) from the lung 1 in the oxygenated blood 6 by blood flow, and from the metabolic consumption of oxygen in the lung tissues themselves. Relative to oxygen carried away from the lung 1 in the oxygenated blood 6, the metabolic oxygen consumption in the lung 1 is insignificant and can therefore be approximated to zero. Thus, the oxygen output from a region of interest in the lung is given to an acceptable approximation by the amount of oxygen carried away in the oxygenated blood 6, which can be expressed as a function of blood flow and the difference between the oxygen concentration in deoxygenated blood 4 and oxygenated blood 6, as set out in equation 8:

$$d\dot{O}_{O_2} = \dot{Q}(Cc_{O_2}' - C\bar{v}_{O_2}) \quad (8)$$

where $d\dot{O}_{O_2}$ is a value representing the amount of oxygen leaving the region of interest in units of ml gas/min/ml lung; $\dot{Q}$ is the blood flow through the region of interest in ml blood/min/ml lung; $C\bar{v}_{O_2}$ is a value representing the systemic venous concentration of oxygen (i.e. that throughout the subject's body) in units of ml gas/ml blood; and $Cc_{O_2}'$ is a value representing the fractional oxygen concentration of the oxygenated blood 6 as it leaves the region of interest in units of ml gas/ml blood. $\dot{Q}$, $C\bar{v}_{O_2}$, $Cc_{O_2}'$ are shown in relation to one another in FIG. 3.

For a given local partial pressure of oxygen, certain concentrations of oxygen are present in the oxygenated blood (both dissolved in blood plasma and bonded to haemoglobin) and in the lung tissues (i.e. in the tissue water). There is a standard solubility coefficient $\alpha_{O_2}$ for oxygen in water. Multiplying the local partial pressure of oxygen by this coefficient gives the concentration of oxygen in the water in units of ml $O_2$/ml blood.

Figure 4:
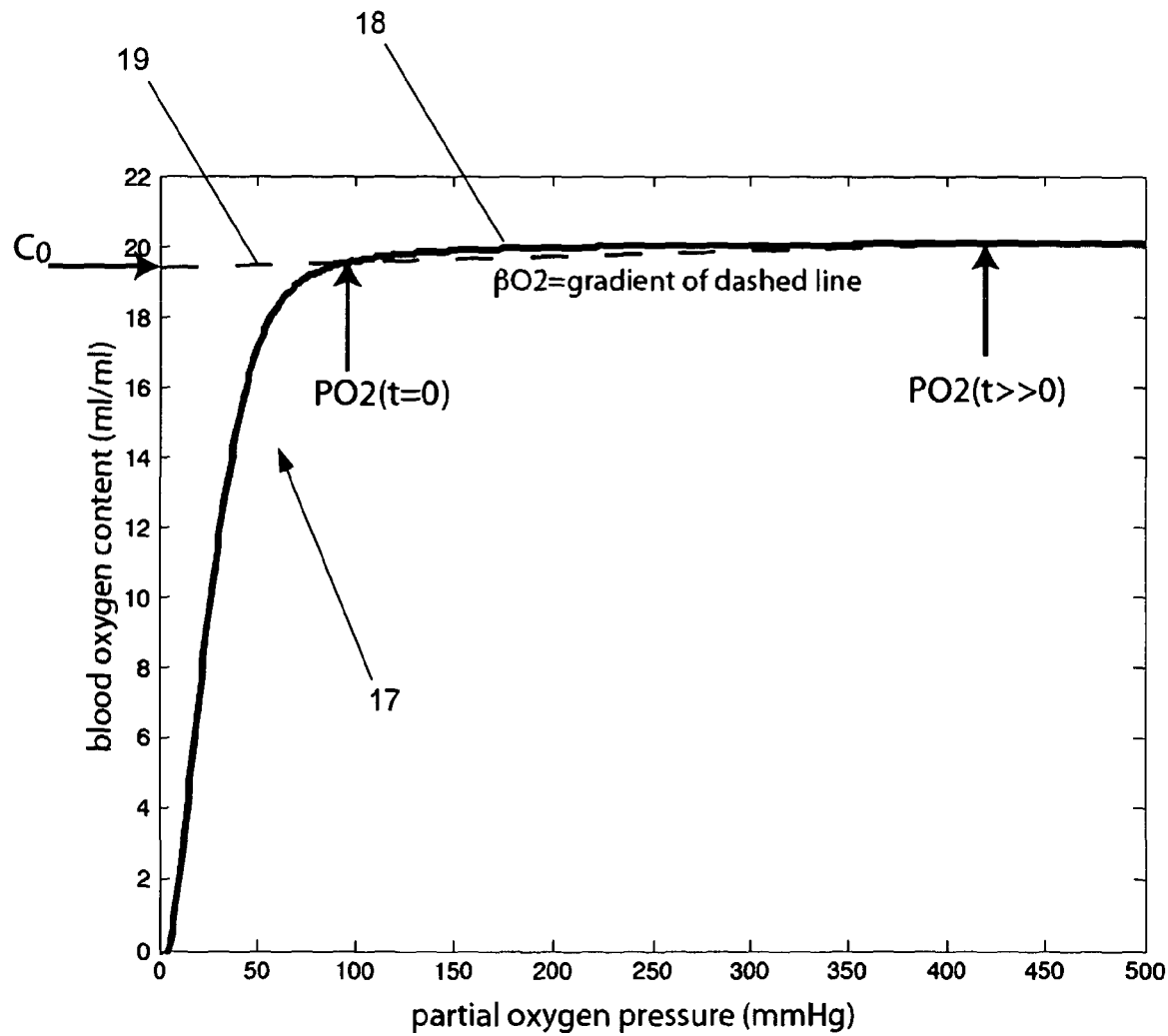
FIG. 4 is an annotated graph representing the dissociation curve for oxygen concentration in blood and a linear approximation of that curve.

The concentration of oxygen $Cc_{O_2}'$ is determined by a dissociation curve 17 such as that shown in FIG. 4, determined empirically by Kelman (JAP 21(4): 1375-6, 1966). It can be seen that the local partial pressure of oxygen is indicated on the x-axis and the concentration of oxygen in the blood is indicated on the y-axis. The portion of the dissociation curve near saturation (above around 20 ml $O_2$/ml blood), marked 18, is almost straight. The dissociation curve is approximated using a straight line 19 (represented in FIG. 4 by a dashed line). The straight line is defined by two constants, constant Co indicating a point at which the straight line 19 meets the y-axis and a gradient of the straight line (i.e. the solubility coefficient $\beta_{O_2}$). It will be appreciated that different straight line approximations (defined by respective values of Co and $\beta_{O_2}$) may be applied in different regions of a lung.

A value of the concentration of oxygen in the blood may be approximated for partial pressures using only the two constants Co and $\beta_{O_2}$ and a value indicating the local partial pressure of oxygen, in this case the partial pressure of dissolved oxygen $Pw_{O_2}$, as set out in equation 9:

$$Cc_{O_2}' = Co + \beta_{O_2} Pw_{O_2} \quad (9)$$

where $Cc_{O_2}'$ is the concentration of oxygen in the blood in ml $O_2$/ml blood; Co is an offset as described above the concentration of oxygen for a zero partial pressure $Pw_{O_2}$ in units of ml $O_2$/ml blood; and $\beta_{O_2}$ is a value representing the solubility coefficient of oxygen in the blood in ml $O_2$/ml blood/mmHg.

In the event that the described linear approximation is insufficiently accurate, such as in the case of severe pathology, it will be appreciated that, instead of approximating the dissociation curve using a linear function it is possible to more closely approximate the curve using a more complex function.

The combined blood and tissues (i.e. the biological material within the region of interest) therefore has a solubility coefficient of its own ($\alpha_{O_2}'$) which is defined in equation 10:

$$\alpha_{O_2}' = \frac{f_B(CO + \beta_{O_2} Pw_{O_2}) f_W \alpha_{O_2} Pw_{O_2}}{Pw_{O_2}} \quad (10)$$

where $f_B$ is the fraction of blood in the space; $f_W$ is the fraction of water in the space; $\beta_{O_2}$ is a standard solubility coefficient for oxygen in blood in units of ml $O_2$/ml blood/mmHg and $\alpha_{O_2}$ is the solubility coefficient of oxygen in water and $Pw_{O_2}$ is the partial pressure of dissolved oxygen.

Taking into account the proportion of a region of interest which is biological material and the solubility coefficient of that biological material, the net change in concentration of oxygen in the blood and tissue water for a given change in partial pressure $Pw_{O_2}$ is given by the input from diffusion less the output from blood flow, which is expressible as equation 3 less equation 8, as set out in equation 11:

$$\alpha_{O_2}' v_W \frac{dPw_{O_2}}{dt} = DM_{O_2}(PA_{O_2} - Pw_{O_2}) - \dot{Q}(Cc_{O_2}' - C\bar{v}_{O_2}) \quad (11)$$

where $\alpha_{O_2}'$ is the solubility coefficient for oxygen into the biological material in the region of interest within the lung, including both tissue water and blood; $v_W$ is the fractional volume of the region of interest which is biological material; and $dPw_{O_2}$ is the difference in partial pressure of oxygen in the region of interest.

Substituting equation 9 into equation 11 gives a mathematical model of the net change in dissolved partial pressure of oxygen in the blood and tissue water in a region of interest in terms of partial pressures, as set out in equation 12:

$$\alpha_{O_2}' v_W \frac{dPw_{O_2}}{dt} = \quad (12)$$
$$DM_{O_2}(PA_{O_2} - Pw_{O_2}) - \dot{Q}(CO + \beta_{O_2} Pw_{O_2} - C\bar{v}_{O_2})$$

As with $F_{I_{O_2}}$, $C\bar{v}_{O_2}$ can conveniently be estimated in units of a fractional volume of oxygen to volume of blood (i.e. fractional concentration) and need not therefore be converted to a partial pressure. If values of $C\bar{v}_{O_2}$ were measured over time by some method then conversion to units of partial pressure may be desirable and can be achieved by performing a substitution into equation 11 using an identity of the kind set out in equation 10, albeit specific to the relationship between the available measurement, the concentration of oxygen in the venous blood $C\bar{v}_{O_2}$ and the partial pressure of oxygen in the venous blood.

It will be appreciated that equations 7 and 12 represent two components of a mathematical model 13 which characterise respectively the transmission of oxygen from an external source which is breathed by the subject into the alveolar spaces in the lung 1 (ventilation, $\dot{V}_I$, which is described above as being is assumed to be equal to the $\dot{V}_A$ term in equation 7) and the transport of oxygen into deoxygenated blood 4 in the lung 1 which is then carried away by the oxygenated blood 6 (perfusion, $\dot{Q}$). It will be appreciated that such a model 13 can advantageously be used to infer measurements of physiological parameters which cannot be measured, or are difficult to measure, directly. The model components 13 have a large number of parameters, any of which may provide useful clinical information provided that reliable values for that parameter can be obtained. One way to produce values for the parameters in a model is to obtain measurements (over time) for a parameter or parameters to the model and find values for the remaining parameters which (when the model is numerically evaluated for each of the modelled values) would produce values similar to, or the same as, those measured for the measured parameter. Another method would be to estimate values for an estimated parameter by some reliable method other than the mathematical model and find values for the other parameters which would produce values similar to the estimated parameters. The method of finding appropriate values for the parameters of the model can be any appropriate method; for example a least squared error fitting algorithm such as the Levenberg-Marquardt algorithm may be used. It will be appreciated that the more parameters in a model which can reliably be measured or estimated, the greater the likelihood of accuracy in the modelled values of the other parameters.

When using the model 13 with OE-MRI data, the concentration of oxygen breathed by the subject (either estimated as $F_{I_{O_2}}$ or measured) is an input to the ventilation model (equation 7). A further input to that model is the partial pressure of dissolved oxygen in a region of interest within the lung tissues and blood, $Pw_{O_2}$, which is input to the model from the 4D dataset of partial pressure values produced by the OE-MRI study described above. For example, a set of data values input to the model might be l(2,3,4,t) where the (x,y,z) co-ordinates of the spatial location within the lungs are (2,3,4) and t represents an acquisition time. Another input to the model could be, for example, the systemic venous concentration of oxygen $C\bar{v}_{O_2}$, which could be estimated from known statistical averages for age and disease groups. Alternatively, $C\bar{v}_{O_2}$ could be measured directly either from the OE-MRI study (by measuring the partial pressure of oxygen in a large vein, such as the vena cava) or by monitoring a patient's blood gases by any other clinically established method.

It will be appreciated that in order to fit equation 12 to values of $Pw_{O_2}$ using a least squared error fitting algorithm it is first necessary to solve equation 12 so that the resulting equation contains a $Pw_{O_2}$ parameter rather than a $dPw_{O_2}$ parameter. Similarly, if values of $PA_{O_2}$ were obtained and used as inputs to the model then equation 7 would need to be solved so as to include a $PA_{O_2}$ term instead of a $dPA_{O_2}$ term. It will be appreciated that there are many methods of solving the equations algebraically to achieve this goal.

Although obtaining more measurements for use as inputs to the model increases the accuracy of the outputs from the model after fitting, it is not always desirable to obtain a number of different measurements for different model parameters over time so as to feed them all into the model. An alternative approach to increasing the accuracy of modelled parameter values resulting from a fit of the model 13 to measured data is to make assumptions about the model or its parameters in the hope of simplifying the models. One possible approach to this, set out immediately below, is tailored to generate a model suitable for fitting to the OE-MRI data and other data derived from measurements and/or estimations so as to generate values of $\dot{V}_A$ and $\dot{Q}$ (respectively ventilation, in units of ml gas/min/ml lung, and perfusion, or blood flow, in units of ml blood/min/ml lung). The resulting values of $\dot{V}_A$ and $\dot{Q}$ may then be analysed individually or combined (e.g. by dividing the value for $\dot{V}_A$ for each region of interest by the corresponding value for $\dot{Q}$) to represent the mismatch between ventilation and perfusion for each of the regions of interest within the lungs. It will be apparent that accurate values for such measurements would be extremely valuable to the clinician in the diagnosis, prognosis and treatment of patients with pulmonary dysfunction, for example patients suffering from COPD. In particular, given that $\dot{V}_A$ represents the volume of air ventilated into a region of interest within the lung over a given time period, and given that all of the lung is being imaged (as a plurality of adjacent regions of interest), if a value can be determined for $\dot{V}_A$ in each region of interest and all of these values for the lungs summed together, then the total should be (at least approximately) equal to the volume of air breathed in by the subject over the same time period. This represents an example of the ways in which the results of the model 13 can be verified by related measurements.

Given that, in any region of interest within a lung, part of the region can be made up of alveolar spaces (the change in oxygen in which is modelled in equation 7) and part made up of tissue and blood spaces (the change in oxygen in which is modelled in equation 11), it can be assumed that everything within the lung may be modelled by either the model component of equation 7 or by the model component of equation 11. It will of course be appreciated that some regions of interest may be entirely alveolar space or entirely lung tissue and blood. Thus, it may be assumed that the fractional volume of biological material $v_W$ in a region of interest and the fractional volume of gaseous alveolar spaces $v_A$ in the region of interest, when summed together, add up to one. This assumption allows equation 7 to be set out as follows in equation 13:

$$\frac{1-v_W}{PB-P_{H_2O}} \frac{dPA_{O_2}}{dt} = \dot{V}_A\left(FI_{O_2} - \frac{PA_{O_2}}{PB-P_{H_2O}}\right) - DM_{O_2}(PA_{O_2} - PW_{O_2}) \quad (13)$$

That is the :identity $v_A=1-v_W$ is used in equation 13 such that everything which is not tissue and blood is considered to be alveolar gas space, and this proportion of the whole may be represented as $(1-v_W)$.

Recalling equation 12:

$$\alpha'_{O_2} v_W \frac{dPW_{O_2}}{dt} = DM_{O_2}(PA_{O_2} - PW_{O_2}) - \dot{Q}(CO + \beta_{O_2} PW_{O_2} - C\bar{v}_{O_2}) \quad (12)$$

Equations 13 and 12 can be combined by addition so as to produce a single equation for a model 13 of the change in the partial pressure of dissolved oxygen in the lung 1 including the parameters of both models, as set out in equation 14:

$$\left(\frac{1-v_W}{PB-P_{H_2O}} \frac{dPA_{O_2}}{dt}\right) + \left(v_W \alpha'_{O_2} \frac{dPW_{O_2}}{dt}\right) = \dot{V}_A\left(FI_{O_2} - \frac{PA_{O_2}}{PB-P_{H_2O}}\right) - \dot{Q}(CO + \beta_{O_2} PW_{O_2} - C\bar{v}_{O_2}) \quad (14)$$

The terms for diffusion in equations 12 and 13 are equal but have opposite sign, and they therefore cancel when equations 12 and 13 are added together as shown in equation 14.

A useful assumption to make is that the partial pressure of oxygen in the alveolar spaces is (at least approximately) equal to the partial pressure of oxygen in the surrounding tissue water and blood. This is a reasonable approximation given that diffusion between the two spaces occurs to correct an imbalance between the partial pressures of oxygen between the two spaces, and that the time scales involved in correcting the imbalance are relatively small. The approximation may not, of course, be appropriate in the case of abnormal lung function resulting in severe impairment of diffusion of oxygen between the alveolar spaces and the biological material in the lungs, e.g. in a subject suffering from severe emphysema or interstitial fibrosis. However Wagner and West (JAP, 33, 62-71, 1972) have shown that the assumption holds true even if diffusion capacity is as low as 25% of normal diffusion capacity. The approximation is set out in equation 15:

$$\text{Assume: } P_{A_{O_2}} = P_{W_{O_2}} \quad (15)$$

where $PA_{O_2}$ represents the partial pressure of oxygen in the alveolar spaces in units of mmHg; and $Pw_{O_2}$ represents the partial pressure of oxygen in the tissue water and blood in units of mmHg.

Equation 14 may therefore be rewritten so the $dPA_{O_2}$ term is replaced by $dPw_{O_2}$, allowing $dPw_{O_2}/dt$ to be factored out of the right hand side of equation 15, as set out in equation 16:

$$\left(\frac{1-v_W}{PB-P_{H_2O}}+v_W\alpha'_{O_2}\right)\frac{dPW_{O_2}}{dt}= \tag{16}$$

$$\dot{V}A\left(FI_{O_2}-\frac{PW_{O_2}}{PB-P_{H_2O}}\right)-\dot{Q}(CO+\beta_{O_2}PW_{O_2}-C\bar{v}_{O_2})$$

which can be written as:

$$\left(\frac{1-(1-\lambda')v_W}{PB-P_{H_2O}}\right)\frac{dPW_{O_2}}{dt}= \tag{17}$$

$$\dot{V}A\left(FI_{O_2}-\frac{PW_{O_2}}{PB-P_{H_2O}}\right)-\dot{Q}(CO+\beta_{O_2}PW_{O_2}-C\bar{v}_{O_2})$$

where $\lambda'=\alpha_{O_2}'(P_B-P_{H_2O})$ is a substitution which has been made for ease of representation, and represents the partition coefficient of oxygen between the gas phase and the blood and tissue water phase expressed in terms of barometric pressure (less water vapour pressure) multiplied by the solubility coefficient of oxygen in the blood and tissue water.

The combined model 13 of equation 17 may be fitted for values of $Pw_{O_2}$ given by the 4D dataset produced by the OE-MRI study described above in the same way as described in relation to equations 7 and 12 but first (as mentioned above) the differential should be solved so that the model has a parameter for $Pw_{O_2}$. This may be achieved using an integrating factor as described below.

Equation 17 is rearranged into a form suitable for application of an integrating factor. Equation 17 is first rewritten by dividing both sides by $$\left(\frac{1-(1-\lambda')v_W}{PB-P_{H_2O}}\right)$$

to give:

$$\frac{dPW_{O_2}}{dt}=\frac{PB-P_{H_2O}}{1-(1-\lambda')v_W} \tag{18}$$

$$\left(\dot{V}A\left(FI_{O_2}-\frac{PW_{O_2}}{PB-P_{H_2O}}\right)-\dot{Q}(CO+\beta_{O_2}PW_{O_2}-C\bar{v}_{O_2})\right)$$

expanding the outermost bracket of the right hand side of equation 18 gives:

$$\frac{dPW_{O_2}}{dt}=\frac{\dot{V}A(PB-P_{H_2O})}{1-(1-\lambda')v_W}\left(FI_{O_2}-\frac{PW_{O_2}}{PB-P_{H_2O}}\right)- \tag{19}$$

$$\frac{\dot{Q}(PB-P_{H_2O})}{1-(1-\lambda')v_W}(CO+\beta_{O_2}PW_{O_2}-C\bar{v}_{O_2})$$

Further expansion gives:

$$\frac{dPW_{O_2}}{dt}=\frac{\dot{V}A(PB-P_{H_2O})FI_{O_2}}{1-(1-\lambda')v_W}- \tag{20}$$

$$\frac{\dot{V}A(PB-P_{H_2O})PW_{O_2}}{1-(1-\lambda')v_W(PB-P_{H_2O})}-\frac{\dot{Q}(PB-P_{H_2O})CO}{1-(1-\lambda')v_W}-$$

-continued
$$\frac{\dot{Q}(PB-P_{H_2O})\beta_{O_2}PW_{O_2}}{1-(1-\lambda')v_W}+\frac{\dot{Q}(PB-P_{H_2O})C\bar{v}_{O_2}}{1-(1-\lambda')v_W}$$

Factoring based on $PW_{O_2}$ and $(PB-P_{H_2O})$ then gives:

$$\frac{dPW_{O_2}}{dt}=-\left(\frac{\dot{V}A}{1-(1-\lambda')v_W}+\frac{\dot{Q}(PB-P_{H_2O})\beta_{O_2}}{1-(1-\lambda')v_W}\right)PW_{O_2}+ \tag{21}$$

$$(PB-P_{H_2O})\left(\frac{\dot{V}AFI_{O_2}}{1-(1-\lambda')v_W}-\frac{\dot{Q}CO}{1-(1-\lambda')v_W}+\frac{\dot{Q}C\bar{v}_{O_2}}{1-(1-\lambda')v_W}\right)$$

Which can be rewritten as:

$$\frac{dPW_{O_2}}{dt}+ \tag{22}$$

$$\left(\frac{\dot{V}A}{1-(1-\lambda')v_W}+\left(\frac{\dot{Q}}{1-(1-\lambda')v_W}\right)\beta_{O_2}(PB-P_{H_2O})\right)PW_{O_2}=$$

$$(PB-P_{H_2O})+\left(\frac{\dot{V}AFI_{O_2}}{1-(1-\lambda')v_W}-\frac{\dot{Q}}{1-(1-\lambda')v_W}(C\bar{v}_{O_2}-CO)\right)$$

when v, q and $\lambda_B$ are defined as follows:

$$v=\frac{\dot{V}A}{1-(1-\lambda')v_W} \tag{23}$$

$$q=\frac{\dot{Q}}{1-(1-\lambda')v_W} \tag{24}$$

$$\lambda_B=\beta_{O_2}(P_B-P_{H_2O}) \tag{25}$$

Allows equation 22 to be rewritten as:

$$\frac{dPW_{O_2}}{dt}+(v+q\lambda_B)PW_{O_2}(t)= \tag{26}$$

$$(P_B-P_{H_2O})(vFI_{O_2}(t)+q(C\bar{v}_{O_2}(t)-CO))$$

The parameters v, q and $\lambda_B$ represent components of the model which are constant, i.e. their values do not change in a particular region of interest within a subject's lungs unless the function of that region of the lung changes. It should be noted that equations 23 and 24 in particular comprise a common denominator together with a parameter respectively representing ventilation ($\dot{V}_A$) and perfusion ($\dot{Q}$). $\lambda_B$ is the partition coefficient of oxygen between the alveolar spaces and the blood (whereas $\lambda'$ is the partition coefficient of oxygen between the alveolar spaces and all of the non-gaseous spaces in the region of interest). In equation 26, the $Pw_{O_2}$, $FI_{O_2}$ and $C\bar{v}_{O_2}$ terms comprise indices of time t. It will be appreciated that values of the lung parameters represented by these terms vary over time and that the terms themselves are functions of time. It will further be appreciated that the indices are implicit in equations 1 to 18 but have been omitted for clarity of representation. The indices are shown in equation 19 and all subsequent equations because they are relevant both to the use if the integrating factor and to the fitting of the model to data values obtained for a plurality of time points Equation 26 is in a standard form required for the application of an integrating factor, the standard form being set out in equation 27:

$$\frac{dy}{dx} + P(x)y = Q(x) \qquad (27)$$

where $$y(x) = PW_{O_2}(t), \qquad (27.1)$$

$$x = t, \qquad (27.2)$$

$$P(x) = v + q\lambda_B, \qquad (27.3)$$

$$Q(x) = (P_B - P_{H_2O})(vFI_{O_2}(t) + qC\bar{v}_{O_2}(t)); \text{ and} \qquad (27.4)$$

$$\frac{dy}{dx} = \frac{dPW_{O_2}}{dt} \qquad (27.5)$$

According to the method of using an integrating factor, equation 27 may be solved by multiplying by an integrating factor $e^{\int P(x)dx}$ and simplifying to give equation 28:

$$\frac{dy e^{\int P(x)dx}}{dx} = Q(x)e^{\int P(x)dx} \qquad (28)$$

Integrating equation 28 gives $$y(x) = \frac{1}{e^{\int P(x)dx}} \int Q(x)e^{\int P(x)dx} dx \qquad (29)$$

Equation 19 may therefore be multiplied by an integrating factor defined as $e^{\int P(x)dx} = e^{\int v+q\lambda_B dt} = e^{(v+q\lambda_B)t}$. Substituting the definitions of 27.1 to 27.5 into equation 29 gives:

$$Pw_{O_2}(t) = e^{-(v+q\lambda_B)t} \int (P_B-P_{H_2O})(vF_{I_{O_2}}(t)+q(C\bar{v}_{O_2}(t)-Co))e^{(v+q\lambda_B)t}dt \qquad (30)$$

Equation 30 can be rewritten as a definite integral because for a given time t the limits are known to be 0 and t, provided that a term for the initial condition $Pw_{O_2}(0)$ is added to the right hand side, as set out in equation 27.

$$Pw_{O_2}(t) = e^{-(v+q\lambda_B)t}(\int_0^t[(P_B-P_{H_2O})(vF_{I_{O_2}}(t')+q(C\bar{v}_{O_2}(t')-Co))e^{(v+q\lambda_B)t'}]dt'+Pw_{O_2}(0)) \qquad (31)$$

where t' is an index between 0 and t within the integration. Equation 31 can be rewritten as set out in equation 32:

$$Pw_{O_2}(t) = \int_0^t[(P_B-P_{H_2O})(vF_{I_{O_2}}(t')+q(C\bar{v}_{O_2}(t')-Co))e^{(v+q\lambda_B)(t'-t)}]dt'+Pw_{O_2}(0)e^{-(v+q\lambda_B)t} \qquad (32)$$

By using the initial condition that $$\frac{dPW_{O_2}}{dt} = 0,$$

given equation (26) $Pw_{O_2}(0)$ can be defined as set out in equation 33:

$$PW_{O_2}(0) = \frac{P_B - P_{H_2O}}{v + q\lambda_B}(vFI_{O_2}(0) + q(C\bar{v}_{O_2}(0) - CO)) \qquad (33)$$

Equation 33 may readily be substituted into equation 32 so as to remove any $Pw_{O_2}$ terms from the left hand side of the equation. Recalling the description of the nature of the input data from OE-MRI, the data represents changes from the initial conditions measured during the baseline measurement at time t=0. It is therefore necessary to derive an equation representing the difference between $Pw_{O_2}(t)$ and the initial condition $Pw_{O_2}(0)$, as set out in equation 34 by subtracting equation 33 into equation 32:

$$P_{W_{O_2}}(t) - P_{W_{O_2}}(0) = \qquad (34)$$

$$\int_0^t \left[(P_B - P_{H_2O})(vFI_{O_2}(t') + q(C\bar{v}_{O_2}(t') - Co))e^{(v+q\lambda_B)(t'-t)}\right] dt' +$$

$$\left(\frac{P_B - P_{H_2O}}{v + q\lambda_B}(vFI_{O_2}(0) + q(C\bar{v}_{O_2}(0) - Co))\right)(e^{-(v+q\lambda_B)t} - 1)$$

Equation 35 can be rewritten as set out in equation 36:

$$\frac{\Delta PW_{O_2}(t)}{P_B - P_{H_2O}} = \qquad (36)$$

$$v\int_0^t e^{(v+q\lambda_B)(t'-t)}\Delta FI_{O_2}(t')dt' + q\int_0^t e^{(v+q\lambda_B)(t'-t)}\Delta C\bar{v}_{O_2}(t')dt'$$

where $$\Delta PW_{O_2}(t) = PW_{O_2}(t) - PW_{O_2}(0);$$

$$\Delta FI_{O_2}(t) = FI_{O_2}(t) - FI_{O_2}(0); \text{ and}$$

$$\Delta C\bar{v}_{O_2}(t) = C\bar{v}_{O_2}(t) - C\bar{v}_{O_2}(0).$$

which may be rewritten as set out in equation 35:

$$Pw_{O_2}(t) - Pw_{O_2}(0) = (P_B - P_{H_2O})v\int_0^t(F_{I_{O_2}}(t') - F_{I_{O_2}}(0))e^{(v+q\lambda_B)(t'-t)}dt' + (P_B - P_{H_2O})q\int_0^t(C\bar{v}_{O_2}(t') - C\bar{v}_{O_2}(0))e^{(v+q\lambda_B)(t'-t)}dt' \qquad (35)$$

During the fitting process the components of equation 36, which are defined in terms of t, are those for which values are measured or estimated at a plurality of time points. $\Delta Pw_{O_2}(t)$ is a function which represents the change in partial pressure of dissolved oxygen above baseline in the region of interest within the lung, which is preferably measured by OE-MRI in which a scan is performed to generate data for each time t. $\Delta FI_{O_2}(t)$ is a function in terms of t which represents the change in fractional concentration of inspired oxygen above baseline. This is preferably estimated (from the known concentrations of gases breathed by the subject) so as to produce a value for each time t. $\Delta C\bar{v}_{O_2}(t)$ is a function which represents the change in partial pressure of oxygen in venous blood as it enters the lungs above baseline. Values of $\Delta C\bar{v}_{O_2}(t)$ may be estimated from known physiological averages for each time t but may alternatively be measured. $v_W$ is the proportion of non-gaseous space to total space in the region of interest and is preferably measured. $v_W$ can be measured using a variety of tomographic density imaging techniques including a standard MR proton density map or helical x-ray computed tomography (CT). These model parameters form the inputs to the model 13. Once the inputs have been determined, values for the constant parameters which make up the constants v, q and $\lambda_B$ (i.e. $\dot{V}_A$ and $\dot{Q}$) and which are not standard values are determined by fitting, preferably using a least squared error approximator such as the Levenberg Marquardt algorithm. It will be appreciated that such an algorithm can operate by evaluating the equation using a variety of test values in place of the unknowns and calculating squared error between the result of the evaluation and the measured values for one or more of the model parameters. The set of test values which produces a minimal, or "least", squared error is then output from the algorithm as the best approximation to values for the unknown model parameters.

It will be appreciated that in order to produce independent values for $\dot{V}_A$ and $\dot{Q}$ it is necessary to determine values of $v_W$ for input to the model. However, if only relative values of $\dot{V}_A$ and $\dot{Q}$ are required, such as $\dot{V}_A/\dot{Q}$, which would be sufficient to identify, for example, ventilation perfusion mismatch, then $v_W$ need not be determined as an input as it cancels as a result of dividing $\dot{V}_A$ by $\dot{Q}$.

A further simplification of the model can be made if it is assumed that the value of $\Delta F_{I_{O_2}}$ is constant after time t=0, i.e. if it is assumed that the change in $\Delta F_{I_{O_2}}$ takes the form of a step function, that the subject goes from breathing one concentration instantaneously to breathing a different concentration at time t=0, and then remains at this different concentration. Assuming that this is the case, equation 36 can be rewritten because the first integral of equation 36 can be integrated to give equation 37:

$$\frac{\Delta Pw_{O_2}(t)}{P_B - P_{H_2O}} = \frac{v}{(v+q\lambda_B)}\Delta F_{I_{O_2}}(1 - e^{-(v+q\lambda_B)t}) + q\int_0^t e^{(v+q\lambda_B)(t'-t)}\Delta C\bar{v}_{O_2}(t')\,dt' \qquad (37)$$

It is not advisable to repeat this simplification for the remaining integral in equation 37 by assuming that $\Delta C\bar{v}_{O_2}$ is constant because this parameter represents the venous concentration of oxygen, which is an important factor and will change throughout at least part of the time of the study. However various substitutions can be made to further simplify the model if desired. $\Delta C\bar{v}_{O_2}$ should therefore be measured or estimated, at least to an approximation, as an input to the model 13 so that the model 13 obtains valuable clinically acceptable values for the parameters $\dot{V}_A$ and $\dot{Q}$.

In general it will be appreciated that any of the models 13 (i.e. at any stage of simplification) described with reference to equations 1 to 37 may be fitted to measured data in the manner described above so as to generate values for unknown model parameters (i.e. model parameters which have not been measured or estimated by some other means).

Results of application of the invention are now described with reference to FIGS. 5 and 6. The model 13 of the first embodiment as set out in equation 33 was used in conjunction with OE-MRI studies in order to compare the lung function of a group of healthy and unhealthy subjects. The unhealthy subjects all suffered from chronic obstructive pulmonary disease (COPD). The healthy subjects were age matched so as to share the age range of the COPD subjects. The healthy subjects had no known pulmonary disorder.

An OE-MRI study was performed on each subject using a Philips Intera 1.5T MRI scanner. Each subject breathed medical air (21% oxygen) and then subsequently breathed 100% oxygen, both at a flow rate of 15 l/min, using a 3-valve Hudson non-rebreathing mask. Care was taken in each case to ensure a tight seal of the mask against the face. Existing research (Boumphrey S M, Morris E A, Kinsella S M. "100% inspired oxygen from a Hudson mask—a realistic goal?" Resuscitation. April 2003; 57(1):69-72) suggests that it should be possible to achieve fractional inspired oxygen concentrations of around 97% with such an arrangement.

For each subject in turn, while the subject breathed the medical air a set of single-slice inversion-recovery half Fourier single shot turbo spin echo (IR-HASTE) scans was performed with a range of inversion times (TI=50, 300, 1100, 2000, 5000 ms) so as to produce a 3D dataset of baseline $R_1$ values. The coronal imaging slice was positioned posteriorly and the data values were acquired for each slice using a 128×128 matrix of locations on the slice. The in-plane field of view was 450×450 mm and the slice thickness was 10 mm. Thus, each location within the resulting dataset represents a 3.5 mm×3.5 mm×10 mm volume region within the subject. The echo time (TE) was 3 ms and the time between pulse sequences (TR) was 5500 ms. The purpose of this first set of data was to determine the baseline longitudinal relaxation time T1 for all locations throughout the lungs of the subject.

The subject was then scanned continuously with a temporal resolution (i.e. time between the start of one scan and the start of the next scan) of 5.5 s using the same IR-HASTE protocol with an inversion time set at 1100 ms so as to produce further 3D datasets for each of a plurality of times t. After the 15$^{th}$ scan, the gas was switched from medical air to 100% oxygen and scanning was continued for a further 6 minutes. A set of IR-HASTE scans was then performed with the same range of inversion times as used for the baseline scans was then acquired while the subject continued to breathe 100% oxygen. The subjects were free breathing throughout the protocol. Subjects tolerated the protocol well with no adverse events.

Prior to fitting of the model of the first embodiment to the data, an image registration algorithm was applied to the data (in accordance with the method described in Naish J H, Parker G J, Beatty P C, Jackson A, Young S S, Waterton J C, Taylor C J. "Improved quantitative dynamic regional oxygen-enhanced pulmonary imaging using image registration." Magnetic Resonance in Medicine. August 2005; 54(2):464-9) in order to correct for respiratory motion between scans. $T_1$-maps were generated for air and oxygen breathing by fitting on a voxel by voxel basis to a standard inversion-recovery equation. The dynamic $T_1$-weighted images were converted first to $T_1$ values using the baseline $T_1$ map as calibration and then to change in partial pressure of oxygen dissolved in the parenchymal tissue water and blood plasma $\Delta Pw_{O_2}(t)$ using the relaxivity constant $r_1 = 2.49 \times 10^{-4}$ (Zaharchuk G, Martin A J, Dillon W P. "Noninvasive imaging of quantitative cerebral blood flow changes during 100% oxygen inhalation using arterial spin-labeling MR imaging." American Journal of Neuroradiology. April 2008; 29(4):663-7) as described above. The mathematical model described above was then fitted to the data in the manner described above in order to extract parameters relating to regional ventilation and perfusion and quantitative ventilation/perfusion ($\dot{V}_A/\dot{Q}$) maps were generated.

Figure 5:
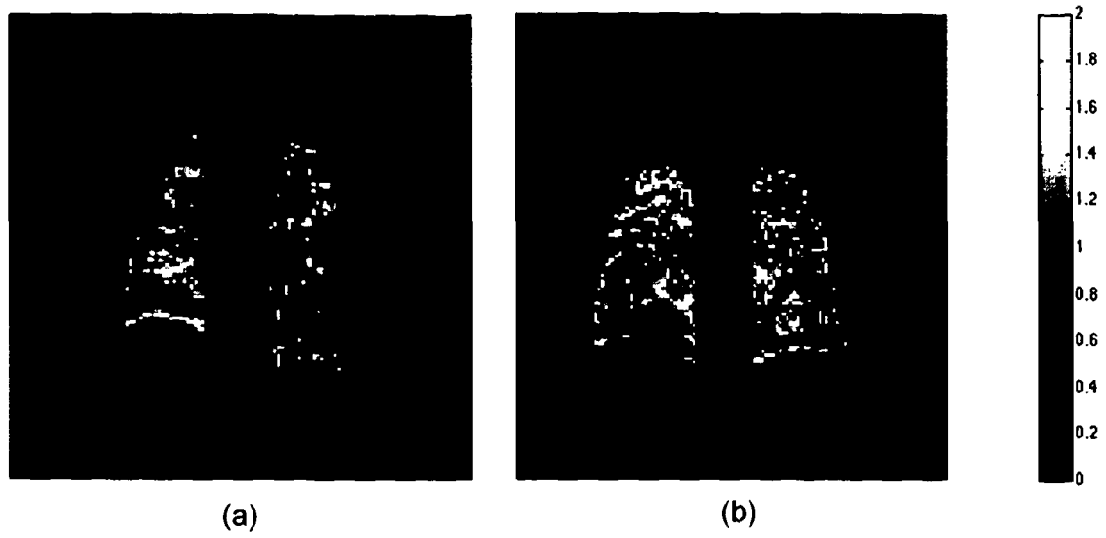
FIG. 5 (*a*) shows a sample ventilation/perfusion map generated using a method according to an embodiment the invention from a healthy subject, and (*b*) the a similar ventilation/perfusion map for a subject suffering from chronic obstructive pulmonary disease (COPD)

FIG. 5 shows example $\dot{V}_A/\dot{Q}$ maps following image registration and model fitting for two subjects of approximately equal age: (a) a healthy volunteer, and (b) a subject with COPD. In the healthy volunteer the $\dot{V}_A/\dot{Q}$ map is relatively uniform across the lungs and in a normal range (around 0.8). In the COPD subject, $\dot{V}_A/\dot{Q}$ is generally lower (shown by darker areas) and appears more spatially heterogeneous (i.e. different regions of the lungs have more widely differing $\dot{V}_A/\dot{Q}$ values than in the healthy volunteer).

Figure 6:
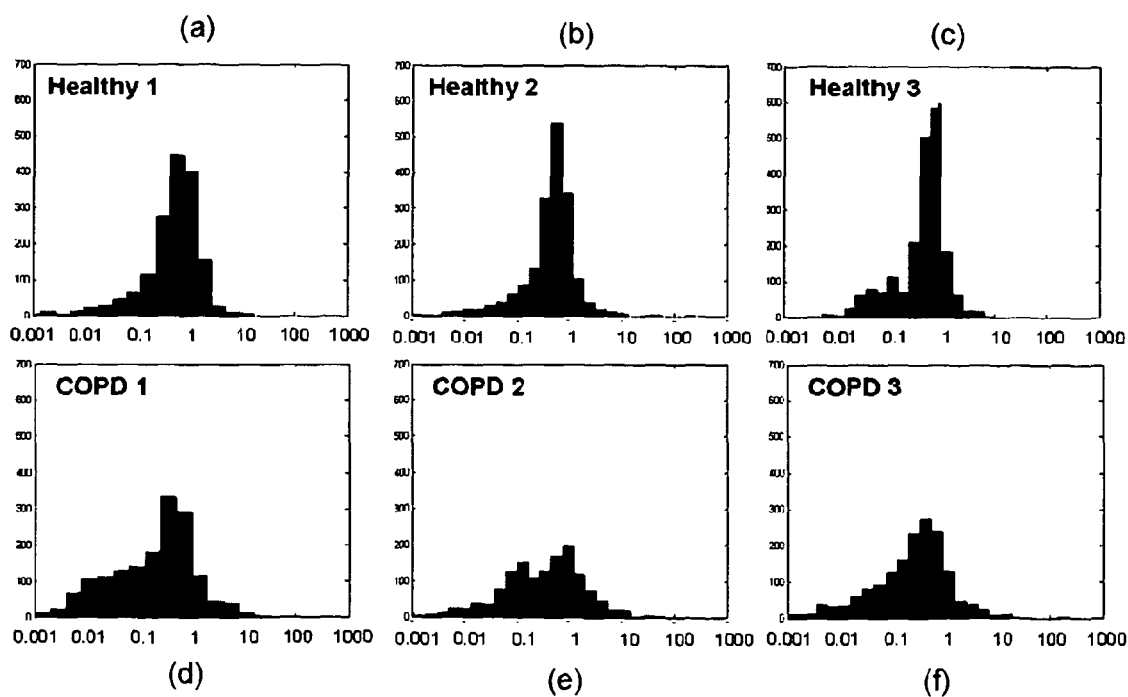
FIG. 6 (*a-c*) show histograms of ventilation/perfusion values for three healthy subjects, and (*d-f*) show histograms of ventilation/perfusion values for three subjects suffering from COPD.

FIG. 6 shows histograms (a-c) for three different subjects with COPD, and (d-f) three healthy volunteers. In each histogram the marks on the x-axis indicate values of $\dot{V}_A/\dot{Q}$ and the marks on the y-axis indicate numbers of locations within the lungs. In the healthy volunteers a narrow peak is observed which indicates that most of the values of $\dot{V}_A/\dot{Q}$ throughout each subject's lungs are similar and cluster around 0.8; in the COPD subjects a broad peak, centered at relatively lower $\dot{V}_A/\dot{Q}$, is observed, which indicates that the values of $\dot{V}_A/\dot{Q}$ throughout the lung are more heterogeneous and that the lungs in general are more poorly ventilated than in the healthy subjects.

It will be appreciated from both FIGS. 5 and 6 that there is basis upon which to make a diagnosis of impaired lung function in the COPD subjects in comparison with the healthy volunteers. Moreover, given that the values of $\dot{V}_A/\dot{Q}$ are in units of ml gas/ml blood, the values themselves represent a quantitative measurement of lung function for each area within the lungs. In general terms it will be appreciated that there may be many clinical uses of such data. It will further be appreciated that the $\dot{V}_A/\dot{Q}$ values may readily be represented as individual values of $\dot{V}_A$ and $\dot{Q}$ for each location within the lungs if a value of $v_W$ can be determined for each location.

It will generally be appreciated that the above described embodiment is merely exemplary and is not intended to limit the scope of the invention. In particular, it will be appreciated that the particular measurements, estimates and assumption used to simplify the model might readily be replaced by other measurements, estimates and assumptions provided that they are clinically acceptable and do not compromise the acceptability of the data output by the model. It will further be appreciated that the model of the function of the lung might derisably be subdivided into different model components and, in some cases, more than two model components.

What is claimed is:

1. A computer-implemented method for assessing a subject's lung, the method comprising:
   receiving, at a processor, first data which has been obtained from the subject by performing Oxygen-Enhanced Magnetic Resonance Imaging (OE-MRI);
   determining, from the first data, a first time-varying input of a partial pressure of oxygen measured in tissue water;
   determining, from the first data, a second time varying input of a partial pressure of oxygen content in inhaled gases;
   determining, from the first data, a third time varying input of oxygen content in venous blood;
   generating, by the processor, an output by fitting a model of lung function to said first time varying input, said second time varying input, and said third time varying input,
   wherein the model of lung function comprises a first model component and a second model component, the first model component having a first input corresponding to said first time varying input of a partial pressure of oxygen measured in tissue water and a second input corresponding to said second time varying input of oxygen content in inhaled gases and modelling a transfer of gaseous oxygen from a gaseous space within the lung to a biological material within the lung, the second model component having an input corresponding to said third time varying input of oxygen content in venous blood and modelling a transfer of oxygen from the lungs by an oxygenation of the venous blood to create oxygenated blood; and
   determining a measure of ventilation and perfusion within the subject's lung based upon said generated output.

2. A method according to claim 1, wherein the second model component comprises a first parameter representing a volume of blood flow.

3. A method according to claim 2 wherein the generated output includes at least one value for said first parameter representing a volume of blood flow.

4. A method according to claim 2 wherein the first model component comprises a second parameter representing a volume of inhaled gases in at least part of the gaseous space.

5. A method according to claim 4 wherein the generated output includes at least one value for said second parameter representing a volume of inhaled gases in at least part of the gaseous space.

6. A method according to claim 4, further comprising generating, by the processor, data based upon said first parameter and second parameter.

7. A method according to claim 6, wherein generating data based upon said first parameter and said second parameter comprises performing, by the processor, an arithmetic operation on a value of said first parameter and a value of said second parameter.

8. A method according to claim 1, wherein said model of lung function models lung function in a part of a lung comprising a first portion comprising said gaseous space and a second portion comprising said biological material.

9. A method according to claim 8, wherein the first model component comprises a second parameter representing a volume of inhaled gases in at least part of the gaseous space, and said first parameter represents a volume of blood flow thorough said second portion of said part of the lung.

10. A method according to claim 8, wherein the first model component comprises a second parameter representing a volume of inhaled gases in at least part of the gaseous space, and said second parameter represents the volume of inhaled gasses in said first portion of said part of the lung.

11. A method according to claim 1, wherein the third time varying input of oxygen content in the venous blood comprises a plurality of values each relating to oxygen content at a respective time.

12. A method according to claim 1, wherein the method further comprises receiving, at the processor, quantitative data indicative of oxygen content in the venous blood having been obtained from the subject.

13. A method according to claim 1, wherein the model includes a parameter representing a solubility of oxygen in blood.

14. A method according to claim 1, wherein the first model component comprises a first part representing an amount of inhaled gases.

15. A method according to claim 14, wherein the first model component further comprises a second part representing an amount of oxygen diffused into the biological material from the gaseous space.

16. A method according to claim 1, wherein the second model component comprises a first part representing the amount of oxygen diffused into the biological material from the gaseous space.

17. A method according to claim 16, wherein the second model component further comprises a second part representing the transfer of oxygen from the lungs by oxygenation of venous blood.

18. A method according to claim 1, wherein the model is based upon an assumption that concentrations of oxygen in the gaseous space within the lung is substantially equal to a concentration of oxygen in the biological material.

19. A method according to claim 1, wherein the model approximates saturation of oxygen in the blood using a linear function.

20. A method according to claim 8, wherein said model comprises a parameter indicating a proportion of said part of the lung made up of one of said first and second portions.

21. A method according to claim 20 further comprising receiving, at the processor, at least one value for the parameter as an input.

22. A method according to claim 21, wherein the at least one value for the parameter has been obtained from the subject.

23. A method claim 20, wherein said first and second components are combined together in the model according to said proportion.

24. A method according to claim 8 wherein the model has the form:

$$\left(\frac{(1-v_W)}{PB-P_{H_2O}} + v_W \alpha'_{O_2}\right)\frac{dPW_{O_2}}{dt} = \dot{V}_A\left(FI_{O_2} - \frac{PW_{O_2}}{PB-P_{H_2O}}\right) - \dot{Q}(CO + \beta_{O_2} PW_{O_2} - C\bar{v}_{O_2})$$

wherein $Pw_{O_2}$ is an input parameter representing the partial pressure of oxygen in the biological material in said part of the lung; $FI_{O_2}$ is an input parameter representing the concentration of oxygen inhaled by the subject; $C\bar{v}_{O_2}$ is an input parameter representing the concentration of oxygen present in the venous system of the subject; $\alpha_{O_2}'$ is an input parameter which represents the solubility of oxygen in the biological material; $\beta_{O_2}$ is an input parameter which represents the solubility coefficient of oxygen in the blood; co is a scalar value; $v_W$, is a parameter representing the proportion of biological material in said part of the lung, $\dot{V}_A$ is an output parameter for the model which represents the volume of inhaled gases within said gaseous space in said part of the lung; and $\dot{Q}$ is an output parameter for the model which represents the volume of blood which passes through said part of the lung.

25. A method according to claim 1, wherein said first time varying input of a partial pressure of oxygen measured in tissue water is magnetic resonance data.

26. A method according to claim 1, wherein said generating the output comprises application of the Levenberg Marquardt non-linear least squares fitting algorithm to the model so as to fit said model to said first data.

27. A computer-implemented method for assessing a subject's lung, the method comprising:
receiving, by a processor, first data obtained from the subject;
determining, from the first data, a first time varying input of a partial pressure of oxygen measured in tissue water;
determining, from the first data, a second time varying input of a partial pressure of oxygen content in inhaled gases;
determining, from the first data, a third time varying input of oxygen content in venous blood;
generating, by the processor, an output by fitting a model of lung function to said first time-varying input, said second time-varying input, and said third time varying input, wherein the model of lung function comprises a first model component and a second model component, the first model component having a first input corresponding to said first time varying input of a partial pressure of oxygen measured in tissue water and a second input corresponding to said second time varying input of oxygen content in inhaled gases and modelling a transfer of gaseous oxygen from a gaseous space within the lung to a biological material within the lung, the second model component having an input corresponding to said third time varying input of oxygen content in venous blood and modelling a transfer of oxygen from the lungs by an oxygenation of the venous blood to create oxygenated blood;
determining a first measure of ventilation and perfusion within the subject's lungs while the subject inhales gases comprising a first concentration of oxygen based upon said generated output;
obtaining, by the processor, a second measure of ventilation within the subject's lung and perfusion within the subject's lung while the subject inhales gases comprising a second concentration of oxygen;
generating, by the processor, second data based upon the first measure and the second measure;
determining, by the processor, a quantitative measure of ventilation within the subject's lung and perfusion within the subject's lung based upon the second data.

28. A method according to claim 27 wherein the first concentration of oxygen is approximately 21% and/or the second concentration of oxygen is approximately 100%.

29. A method according to claim 27, wherein obtaining the first data includes obtaining the first data by performing-magnetic resonance imaging.

30. A method according to claim 27, wherein determining the quantitative measure of ventilation within the subject's lung and perfusion within the subject's lung comprises processing, by the processor, the second data using a mathematical model.

31. A method according to claim 30 wherein the processing comprises determining, by the processor, at least one value of a parameter of the mathematical model based upon said second data.

32. A method according to claim 30, wherein the mathematical model comprises a first model component modelling transfer of a gaseous oxygen from a gaseous space within the lung to a biological material within the lung based upon a first quantitative data indicative of oxygen content in inhaled gases and oxygen content in the biological material and a second model component modelling a transfer of oxygen from the lungs by an oxygenation of venous blood to create an oxygenated blood based upon a second quantitative data indicative of oxygen content in the venous blood.

33. A computer program adapted to implement a method for assessing a subject's lung, the computer program carried by a computer readable medium, the computer program comprising:
computer readable instructions arranged to cause a computer to
receive first data obtained from the subject;
determine, from the first data, a first time varying input of a partial pressure of oxygen measured in tissue water;
determine, from the first data, a second time varying input of a partial pressure of oxygen content in inhaled gases;
determine, from the first data, a third time varying input of oxygen content in venous blood;
generate an output by fitting a model of lung function to said first time varying input, said second time varying input, and second third time varying input,
wherein the model of lung function comprises a first model component and a second model component, the first model component having a first input corresponding to said first time varying input of a partial pressure of oxygen measured in tissue water and a second input corresponding to said second time varying input of oxygen content in inhaled gases and modelling a transfer of a gaseous oxygen from a gaseous space within the lung to a biological material within the lung, the second model component having an input corresponding to third time varying input of oxygen content in venous blood and modelling a transfer of oxygen from the lungs by an oxygenation of the venous blood to create an oxygenated blood; and
determining a measure of ventilation and perfusion within the subject's lung based upon said generated output.

34. An apparatus for assessing a subject's lung, the apparatus comprising:
  a memory storing processor readable instructions; and
  a processor arranged to read and execute instructions stored in said program memory;
  wherein said processor readable instructions comprise instructions arranged to cause the processor to
  receive first data obtained from the subject;
  determine, from the first data, a first time varying input of a partial pressure of oxygen measured in tissue water;
  determine, from the first data, a second time varying input of a partial pressure of oxygen content in inhaled gases;
  determine, from the first data, a third time varying input of oxygen content in venous blood;
  generate an output by fitting a model of lung function to said first time varying input, said second time varying input, and said third time varying input,
  wherein the model of lung function comprises a first model component and a second model component, the first model component having a first input corresponding to said first time varying input of a partial pressure of oxygen measured in tissue water and a second input corresponding to said second time varying input of oxygen content in inhaled gases and modelling a transfer of a gaseous oxygen from a gaseous space within the lung to a biological material within the lung, the second model component having an input corresponding to said third time varying input of oxygen content in venous blood and modelling a transfer of oxygen from the lungs by an oxygenation of the venous blood to create an oxygenated blood; and
  determining a measure of ventilation and perfusion within the subject's lung based upon said generated output.

* * * * *